(12) United States Patent  (10) Patent No.: US 8,829,394 B2
Limaye  (45) Date of Patent: Sep. 9, 2014

(54) MEDICAL NEEDLE REMOVAL AND STORAGE DEVICE

(75) Inventor: Amit U Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 203 days.

(21) Appl. No.: 13/067,535

(22) Filed: Jun. 8, 2011

(65) Prior Publication Data

US 2012/0311839 A1  Dec. 13, 2012

(51) Int. Cl.
*A61M 5/32* (2006.01)

(52) U.S. Cl.
USPC .............................. 219/201; 219/68; 206/365

(58) Field of Classification Search
USPC ........... 219/243, 385, 68, 69.1, 201; 206/364, 206/365, 366
See application file for complete search history.

(56) References Cited

U.S. PATENT DOCUMENTS

| | | | |
|---|---|---|---|
| 2,693,521 A * | 11/1954 | Alexander | 373/112 |
| 4,867,309 A | 9/1989 | Germain | |
| 4,877,934 A | 10/1989 | Spinello | |
| 4,965,426 A | 10/1990 | Colombo | |
| 5,075,529 A | 12/1991 | Kudo | |
| 5,076,178 A | 12/1991 | Kohl et al. | |
| 5,212,362 A | 5/1993 | Burden et al. | |
| 5,245,935 A * | 9/1993 | Fukuda | 110/250 |
| 5,276,297 A * | 1/1994 | Nara | 219/121.43 |
| 5,277,868 A * | 1/1994 | Langford | 422/21 |
| 5,282,428 A | 2/1994 | Greville et al. | |
| 5,417,659 A * | 5/1995 | Gaba | 604/110 |
| 5,545,869 A | 8/1996 | Piva | |
| 5,588,966 A * | 12/1996 | Atsumi | 604/110 |
| 5,741,230 A * | 4/1998 | Miller | 604/110 |
| 5,852,267 A | 12/1998 | Yanobu | |
| 6,036,671 A * | 3/2000 | Frey | 604/110 |
| 6,148,742 A * | 11/2000 | Constable et al. | 110/250 |
| 6,545,242 B1 * | 4/2003 | Butler | 219/68 |
| 7,015,421 B2 * | 3/2006 | Nakagawa | 219/243 |
| 8,201,314 B2 * | 6/2012 | Miller et al. | 29/426.5 |
| 8,201,323 B2 * | 6/2012 | Miller et al. | 29/801 |
| 8,522,974 B2 | 9/2013 | Phan | |
| 2003/0010754 A1 * | 1/2003 | Adkins | 219/69.15 |
| 2005/0121343 A1 * | 6/2005 | Miller et al. | 206/366 |
| 2008/0021387 A1 * | 1/2008 | Gaba et al. | 604/110 |
| 2011/0060292 A1 | 3/2011 | Schraga | |

FOREIGN PATENT DOCUMENTS

| | | |
|---|---|---|
| EP | 0476823 | 2/1995 |
| EP | 1300170 | 12/2005 |
| FR | 2714836 A1 * | 7/1995 |
| GB | 2211420 A * | 7/1989 |
| WO | 2011034576 A1 | 3/2011 |

* cited by examiner

*Primary Examiner* — Henry Yuen
*Assistant Examiner* — John J Norton
(74) *Attorney, Agent, or Firm* — Roylance, Abrams, Berdo & Goodman, L.L.P.

(57) ABSTRACT

An apparatus for removing a needle from a needle holder, including a grasping unit for selectively grasping the needle; a receiving unit for receiving the needle holder, displaceably disposed relative to the grasping unit; a biasing member biasing the receiving unit in a first direction; and separating means for separating the entire needle from the needle holder. Preferably, the needle is heated to melt, soften, or otherwise weaken a material and/or adhesive connecting the needle with the needle holder. Preferably the heating is electrical heating, including completing an electrical circuit through the needle and passing current through the needle, and/or passing current through a heating element.

13 Claims, 25 Drawing Sheets

TOTAL RESISTANCE = (R1 + R2)

(PORTION OF NEEDLE 10 COMPLETING CIRCUIT + 496)

TOTAL RESISTANCE = R1 + $\left(\frac{R2 \times R3}{R2 + R3}\right)$

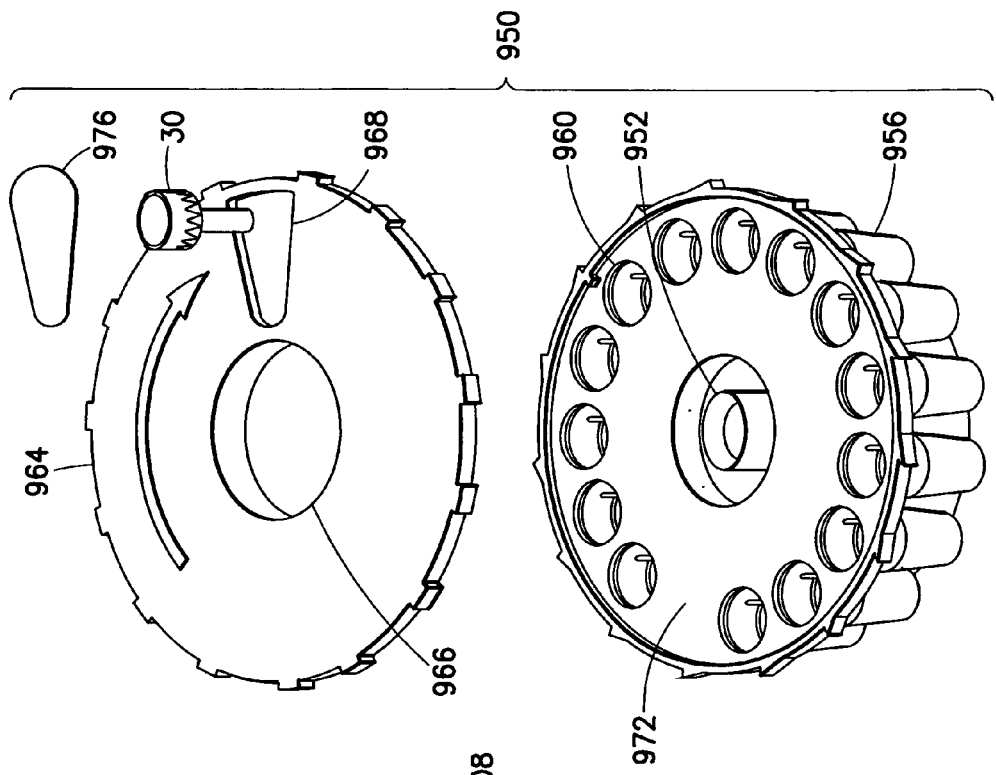
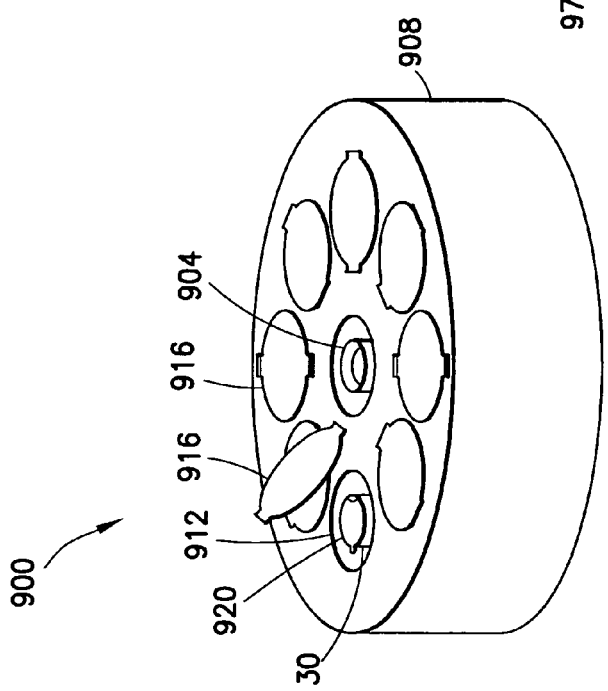
FIG. 34
FIG. 33

MEDICAL NEEDLE REMOVAL AND STORAGE DEVICE

FIELD OF THE INVENTION

The present invention relates generally to a device for removing medical needles and storing the removed needles.

BACKGROUND OF THE INVENTION

After a needle, such as a hypodermic needle, or a pen needle has been used for an injection, it is desirable to remove and store the needle in a safe container. A sharps container for storing needles, which is known in the art, includes an inner box member and an outer housing member. The box and the housing each have an aperture that is dimensioned to receive a hypodermic needle. The box and the housing are hingedly connected to each other so that in an open position the apertures of the box and the housing overlap and the needle may be inserted through both of the apertures to project into the box. After the needle has been inserted into the apertures, the box and the housing are moved with respect to each other, for example in a scissor motion, so that the needle is clipped. After being clipped, the needle drops into the box for storage and subsequent disposal.

U.S. Pat. No. 6,545,242 to Butler discloses a device that, subsequent to insertion of a portion of a needle, heats at least a portion of the needle to approximately 1750° C., and then shears the needle, leaving a portion in the needle holder or hub. Similarly, U.S. Pat. No. 5,545,869 to Piva discloses a device that melts a portion of a blade or needle and cuts the stump of the blade or needle, leaving a portion of the blade or needle in the needle/blade holder or hub. Additionally, U.S. Pat. No. 4,867,309 to Germain discloses a device that holds a needle and its holder or hub by the needle stem, so that a user can twist the hub off of a syringe, or pull off the hub if the hub is friction-fitted on the syringe.

With each of these devices, however, a portion of the needle remains in the needle holder. Therefore, the potential for a needle-stick injury may remain. Additionally, the needle holder must be disposed of as medical waste, and cannot be recycled. Consequently, an improved medical needle removal device that removes the needle entirely is desirable. Storage of the removed needles is also desirable.

SUMMARY OF THE INVENTION

An aspect of the present invention is to provide a device for removing and storing medical needles.

The foregoing and/or other aspects of the present invention are achieved by providing an apparatus for removing a needle from a needle holder, including a grasping unit for selectively grasping the needle; a receiving unit for receiving the needle holder, displaceably disposed relative to the grasping unit; a biasing member biasing the receiving unit in a first direction; and separating means for separating the entire needle from the needle holder.

The foregoing and/or other aspects of the present invention are also achieved by providing a method of separating a needle from a needle holder, including receiving the needle holder in a receiving unit biased in a first direction; displacing the receiving unit relative to a grasping unit in a second direction opposite to the first direction, thereby automatically causing the grasping unit to grasp the needle and activating a separator for separating the needle from the needle holder; and maintaining the grasp of the needle until the separator separates the entire needle from the needle holder.

The foregoing and/or other aspects of the present invention are also achieved by providing an apparatus for removing a needle from a needle holder, including a grasping unit for selectively grasping the needle; a receiving unit for receiving the needle holder, displaceably disposed relative to the grasping unit; a biasing member biasing the receiving unit in a first direction; a separator for separating the entire needle from the needle holder; and a storage unit for storing the separated needle.

The foregoing and/or other aspects of the present invention are also achieved by providing a method of separating a needle adhered to and/or molded in a needle holder, including heating the needle to melt, soften, or otherwise weaken a material and/or adhesive connecting the needle with the needle holder; and separating the entire needle from the needle holder.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 33 is a perspective view of another pen needle dispenser with a needle removal and storage device in accordance with an embodiment of the present invention disposed thereon; and FIG. 34 is a perspective view of another pen needle dispenser with a needle removal and storage device in accordance with an embodiment of the present invention disposed thereon.

DETAILED DESCRIPTION OF EXEMPLARY EMBODIMENTS

Figure 1:
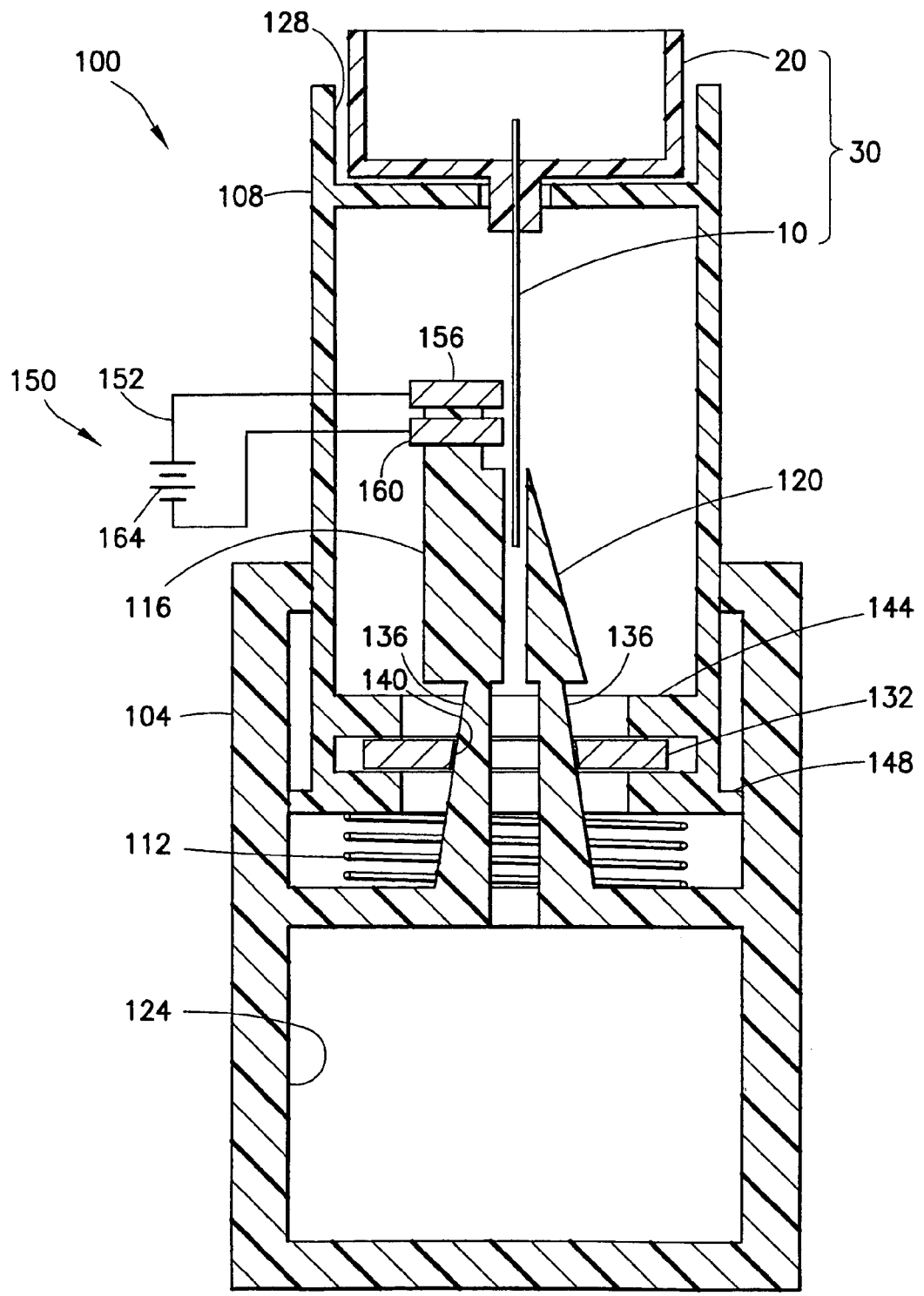
FIG. 1 is a cross-sectional schematic view of a needle removal and storage device in accordance with an embodiment of the present invention.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Descriptions of directions, such as upward, downward, axially, and radially are used herein for reference purposes, but are not limiting. Additionally, for brevity, the word "needle" is used herein to represent a needle, a cannula, or a capillary used in a medical device. Typically, an adhesive is used to adhere a needle to a needle holder. For example, as shown in FIG. 1, a needle 10 is adhered to a needle holder or hub 20, forming a pen needle 30 for attachment to the end of a pen injection device. The metal needle is held in the hub of the pen needle or syringe using a commercially available adhesive (e.g., UV or heat curable epoxies). Alternatively, a needle may be embedded without an adhesive in a plastic needle holder during a molding process. Examples of materials for the needle holder include polyethylene and polypropylene.

Figure 2:
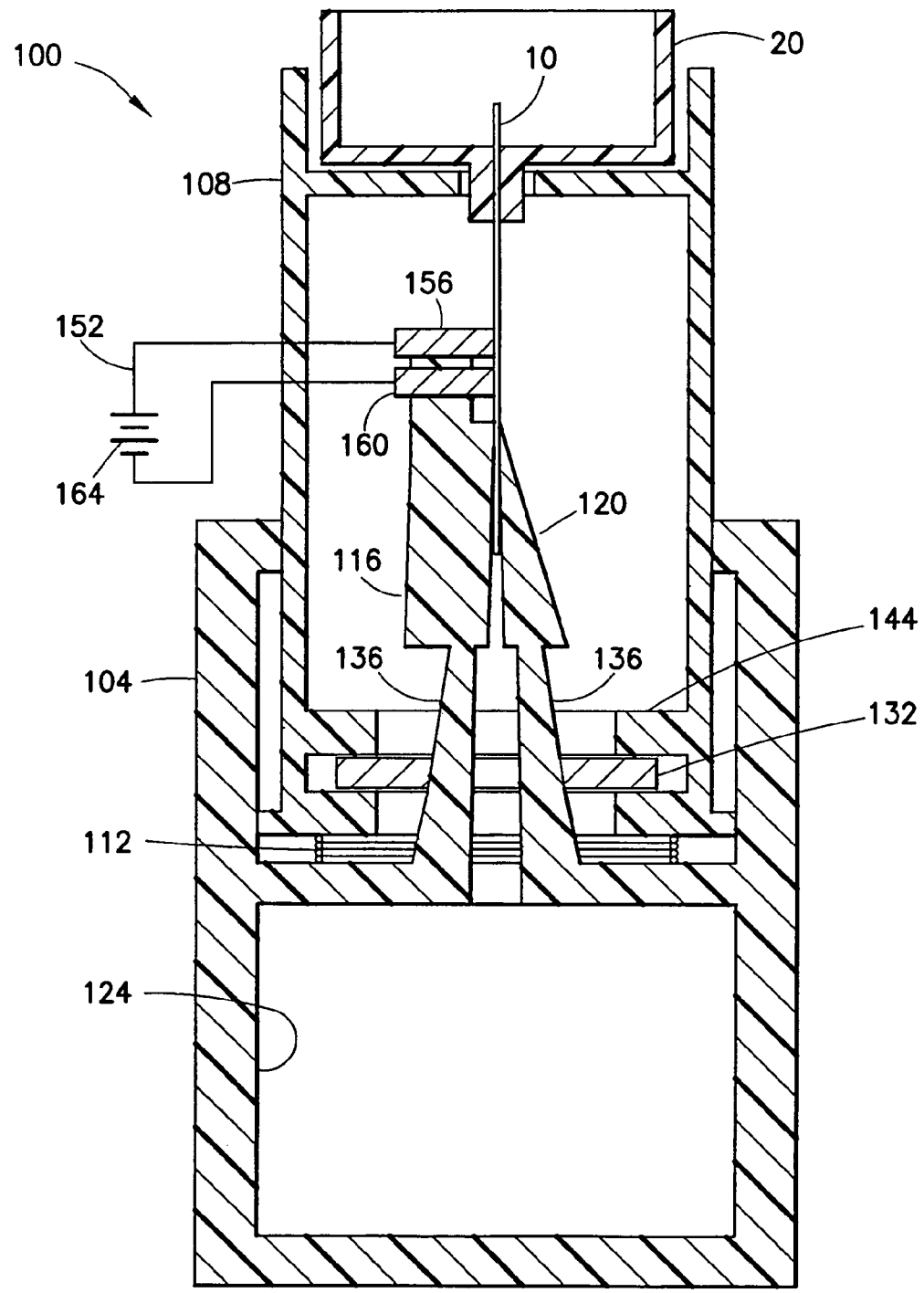
FIG. 2 is a cross-sectional schematic view of the device of FIG. 1 in operation.

FIGS. 1 and 2 are cross-sectional schematic views of a needle removal and storage device 100 in accordance with an embodiment of the present invention. The device 100 includes a grasping unit 104, a receiving unit 108 displaceably disposed relative to the grasping unit 104, and a biasing unit 112. According to one embodiment, the biasing unit 112 is a spring 112. One skilled in the art will appreciate that other biasing units maybe employed without departing from the scope of the present invention. The biasing unit 112 biases the receiving unit 108 in a first direction. In addition, the receiving unit 108 includes a wing 148 for limiting displacement of the receiving unit 108 in the first direction.

The grasping unit 104 includes first and second forceps-like arms 116 and 120, and a storage unit 124. The receiving unit 108 includes a receiving portion 128 for receiving the needle holder 20, and an activating unit 132 for automatically causing the first and second arms 116 and 120 to grasp the needle 10 upon displacement of the receiving unit 108 in a second direction opposite to the first direction.

According to one embodiment, the first and second arms 116 and 120 each have a tapered portion 136 and the activating unit 132 has a corresponding tapered portion 140 on an internal portion thereof. According to one embodiment, the activating unit 132 includes an annular disk held between a pair of supporting arms 144 of the receiving unit 108. The interior of the annular disk 132 includes the tapered portion 140. The activating unit 132 may be made of plastic or metal, such as stainless steel. According to another embodiment, the activating unit 132 and the receiving unit 108 are integrally formed as a unitary construction.

The device 100 also includes separating means 150 for separating the entire needle 10 from the needle holder 20. In the embodiment of FIGS. 1 and 2, the separating means 150 includes the electrical circuit 152 completed by the needle 10. Electrical circuit 152 includes first and second electrical contacts 156 and 160 disposed on the first arm 116. In addition, the electrical circuit 152 includes a power source 164 schematically represented as an ideal voltage source or ideal battery 164.

Although the power source 164 is not depicted as being disposed on either the grasping unit 104 or the receiving unit 108, it will be understood by one skilled in the art that the power source 164 may be disposed on the grasping unit 104 or the receiving unit 108 without departing from the scope of the present invention. Additionally, according to one embodiment, the power source 164 may be a stand-alone unit. Further, although the power source 164 may be a portable DC power source such as a battery (for example, AA, 9V, or rechargeable battery), one skilled in the art will appreciate that other power sources may also be employed, such as an AC wall receptacle or the electrical system of an automobile (for example, an ambulance) without departing from the scope of the present invention.

Referring to FIGS. 1 and 2, to use the device 100, the user places the needle holder 20 of the pen needle 30 into the receiving portion 128 of the receiving unit 108 and then presses downwardly (second direction) on the receiving unit 108. As the user presses down the receiving unit 108, compressing the biasing unit 112, the tapered portion 140 of the activating unit 132 slidingly contacts the tapered portions 136 of the first and second arms 116 and 120, forcing the ends of the arms 116 and 120 together, away from their initial spaced-apart positions, to grasp the needle 10. The downward (second direction) motion of the receiving unit 108 continues until the tapered portion 140 wedges against the tapered portions 136 and the first and second arms 116 and 120 firmly grasp the needle 10. This wedging action effectively temporarily locks the receiving unit 108 relative to the grasping unit 104.

In addition, as the first and second arms 116 and 120 grasp the needle 10, the first and second electric contacts 156 and 160 contact the needle 10, completing the electrical circuit 152 through the needle 10. The needle 10 acts as a resistive element in the electrical circuit 152 and heats up upon completion of the electrical circuit 152 due to the current flow through the needle 10. This heating melts, softens, or otherwise weakens the adhesive adhering the needle 10 to the needle holder 20, or if the needle 10 is embedded into the needle holder 20 during molding without an adhesive, the heating melts, softens, or otherwise weakens the plastic of the needle holder 20 surrounding the needle 10. Because of the melting, softening, or weakening, the biasing unit 112 displaces the receiving unit 108 upwardly (first direction), thereby displacing the needle holder 20 relative to the needle 10, which temporarily remains grasped by the first and second arms 116 and 120, and separating the entire needle 10 from the needle holder 20.

As the biasing unit 112 continues to displace the receiving unit 108 in the first direction, the contact between the tapered portion 140 of the activating unit 132 and the tapered portions 136 of the first and second arms 116 and 120 decreases. Thus, after the needle 10 is separated from the needle holder 20, the first and second arms return to their initial spaced-apart positions and the needle 10 drops into the storage unit 124. At this point, the user can recycle or dispose of the needle holder 20 in the regular trash without any threat of needle-stick injury.

The device 100 depicted in FIGS. 1 and 2 illustrates the first and second electrical contacts 156 and 160 as being spaced apart from the joint between the needle 10 and the needle holder 20 for clarity. Preferably, however, the first and second electrical contacts 156 and 160 contact the needle 10 in close proximity to the joint between the needle 10 and the needle holder 20, to minimize the amount of heating necessary to melt, soften, or weaken the glue joint and/or material holding the needle 10 to the needle holder 20. Additionally, although first and second arms 116 and 120 are illustrated, one skilled in the art will appreciate that a greater number of arms or an arm and anvil configuration may be employed without departing from the scope of the present invention.

According to one embodiment, the device 100 is approximately the size of a lipstick container. Additionally, according to one embodiment, the device 100 includes an indicator, such as an indicator light that alerts the user when the storage unit 124 has reached a certain capacity. Further, according to one embodiment, the device 100 includes a similar feature to manage power requirements, such as indicating the need for battery replacement or recharging.

Figure 3:
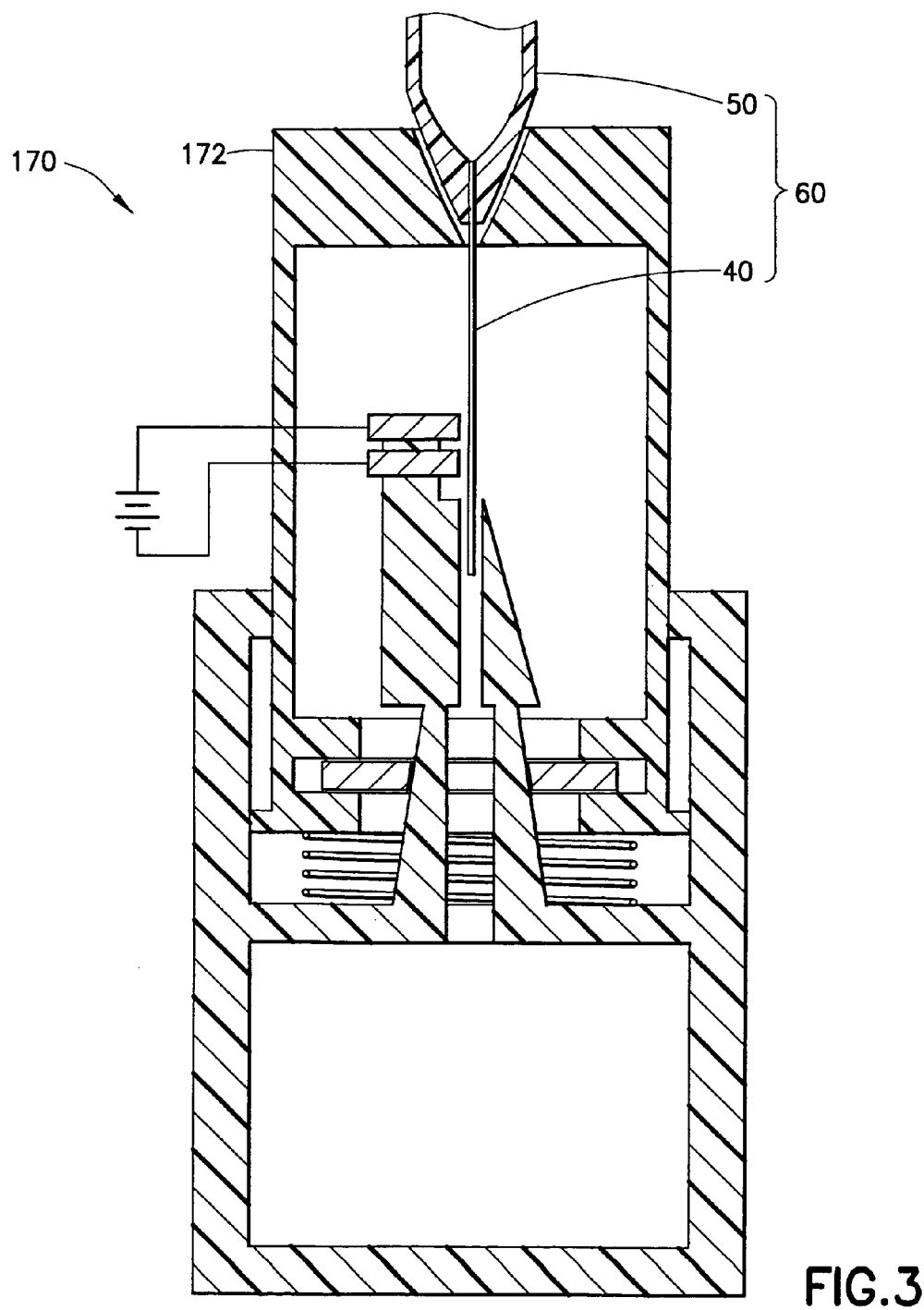
FIG. 3 is a cross-sectional schematic view of a needle removal and storage device in accordance with another embodiment of the present invention.

FIG. 3 is a cross-sectional schematic view of a needle removal and storage device 170 in accordance with another embodiment of the present invention. The device 170 is substantially similar to the device 100 shown in FIGS. 1 and 2, except that receiving unit 172, rather than receiving a hub of a pen needle, instead receives a hub or needle holder 50 that, in conjunction with a needle 40, forms a syringe needle 60.

Figure 4:
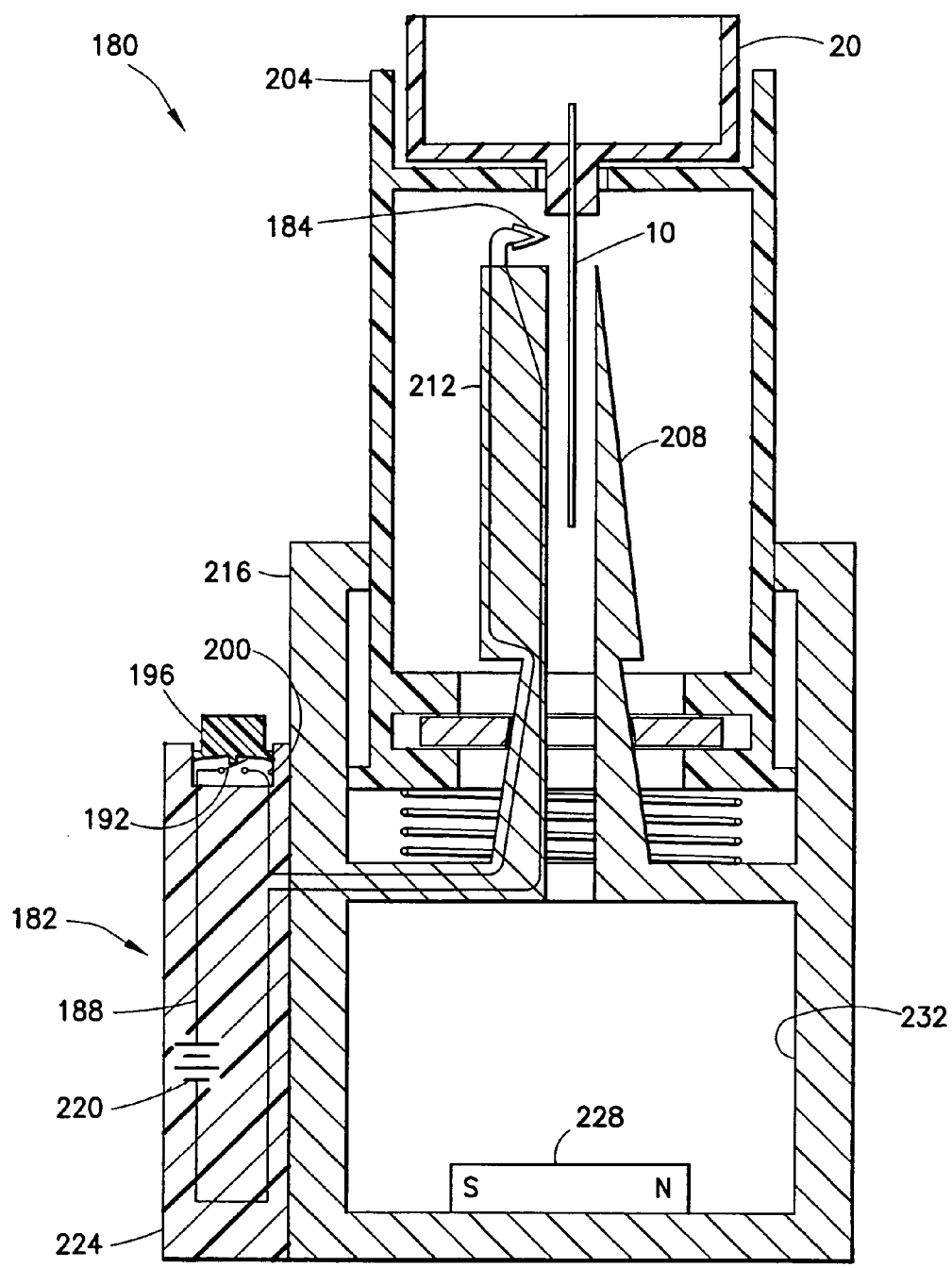
FIG. 4 is a cross-sectional schematic view of a needle removal and storage device in accordance with another embodiment of the present invention.

FIG. 4 is a cross-sectional schematic view of needle removal and storage device 180 in accordance with another embodiment of the present invention. In contrast to the embodiments of FIGS. 1-3, rather than electrical contacts, the device 180 includes a heating element 184. The heating element 184 may be, for example, an appropriately selected high-resistance nichrome wire 184. Moreover, rather than passing current through the needle 10, the heating element 184 contacts and directly heats the needle 10, thereby melting, softening, or otherwise weakening the glue or adhesive joint and/or material holding the needle 10 to the needle holder 20.

The device 180 also includes separating means 182 that includes an electrical circuit 188. The electrical circuit 188 includes a heating element 184 and a switch 192. According to one embodiment, after depressing the receiving unit 204 so that the first and second arms 208 and 212 of the grasping unit 216 grasp the needle 10 and bring the heating element 184 into direct contact with the needle 10, the user activates the switch 192 and completes the electrical circuit 188. The user activates the switch 192 by pressing a button 196, which is biased upwardly by a second biasing unit 200, such as a leaf spring. Completing the electrical circuit 188 passes current through the heating element 184, thereby directly heating the needle 10 to melt, soften, or weaken the adhesive joint and/or material holding the needle 10 to the needle holder 20.

In the embodiment shown in FIG. 4, a power source 220 is disposed within a housing 224 connected to the grasping unit 216. In addition, the device 180 includes a magnet 228 disposed within a storage unit 232. Once separated from the needle holder 20, the magnet 228 attracts the needle 10 into the storage unit 232, and thus, the device 180 is not dependent upon gravity to move the needle 10 into the storage unit 232. One skilled in the art will appreciate that the receiving unit 204 may be configured to receive a syringe needle or other medical needle rather than the pen needle depicted in FIG. 4 without departing from the scope of the present invention.

Figure 5:
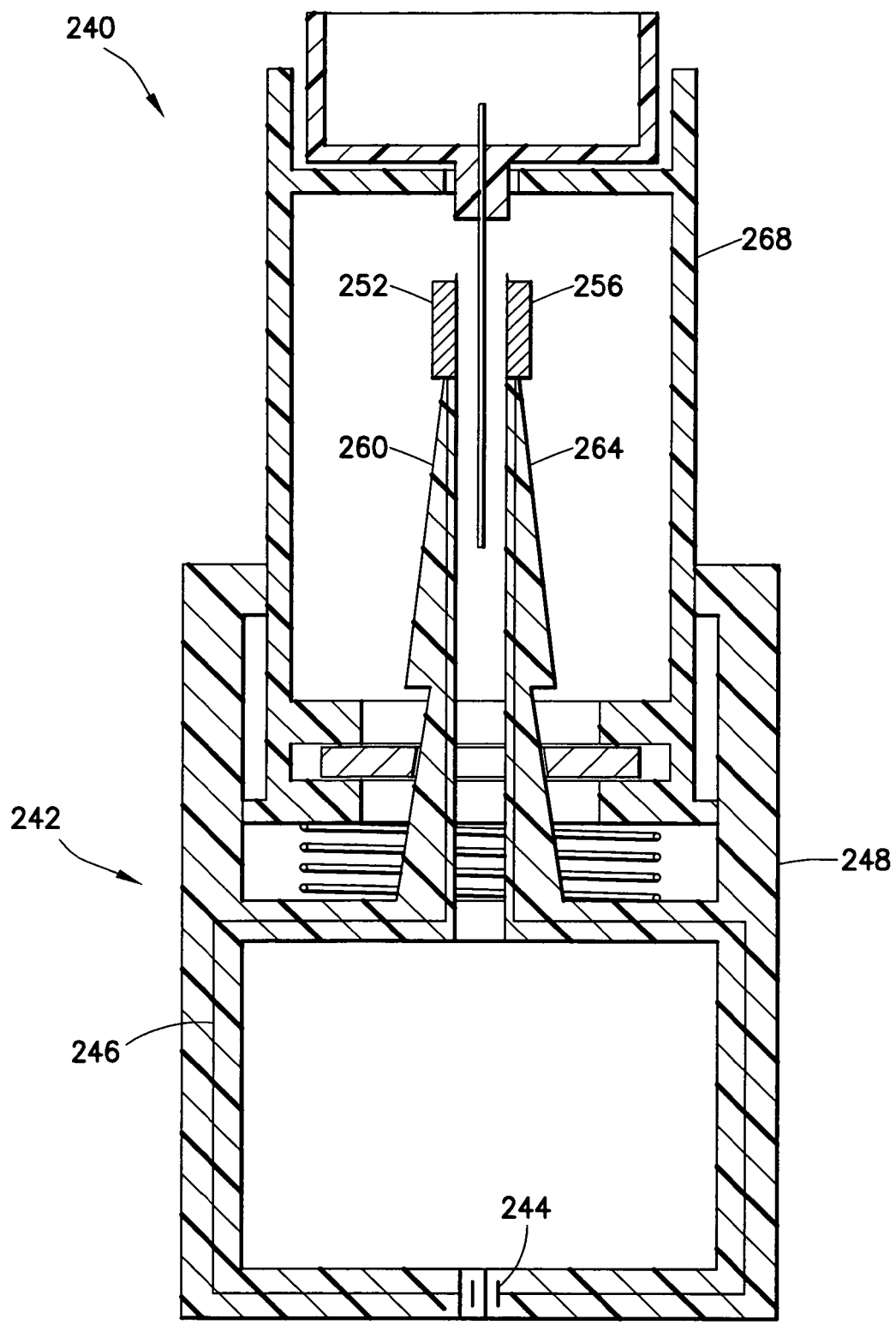
FIG. 5 is a cross-sectional schematic view of a needle removal and storage device in accordance with another embodiment of the present invention.

FIG. 5 is a cross-sectional schematic view of needle removal and storage device 240 in accordance with another embodiment of the present invention. The device 240 is substantially similar to the device 100 illustrated in FIGS. 1 and 2, except that the power source 244 is disposed within the grasping unit 248, and the first and second electrical contacts 252 and 256 are respectively disposed on first and second arms 216 and 264 of the grasping unit 248. The device 240 includes separating means 242 that includes an electrical circuit 246. One skilled in the art will appreciate that the receiving unit 268 may be configured to receive a syringe needle or other medical needle rather than the pen needle depicted in FIG. 5 without parting from the scope of the present invention.

Figure 6:
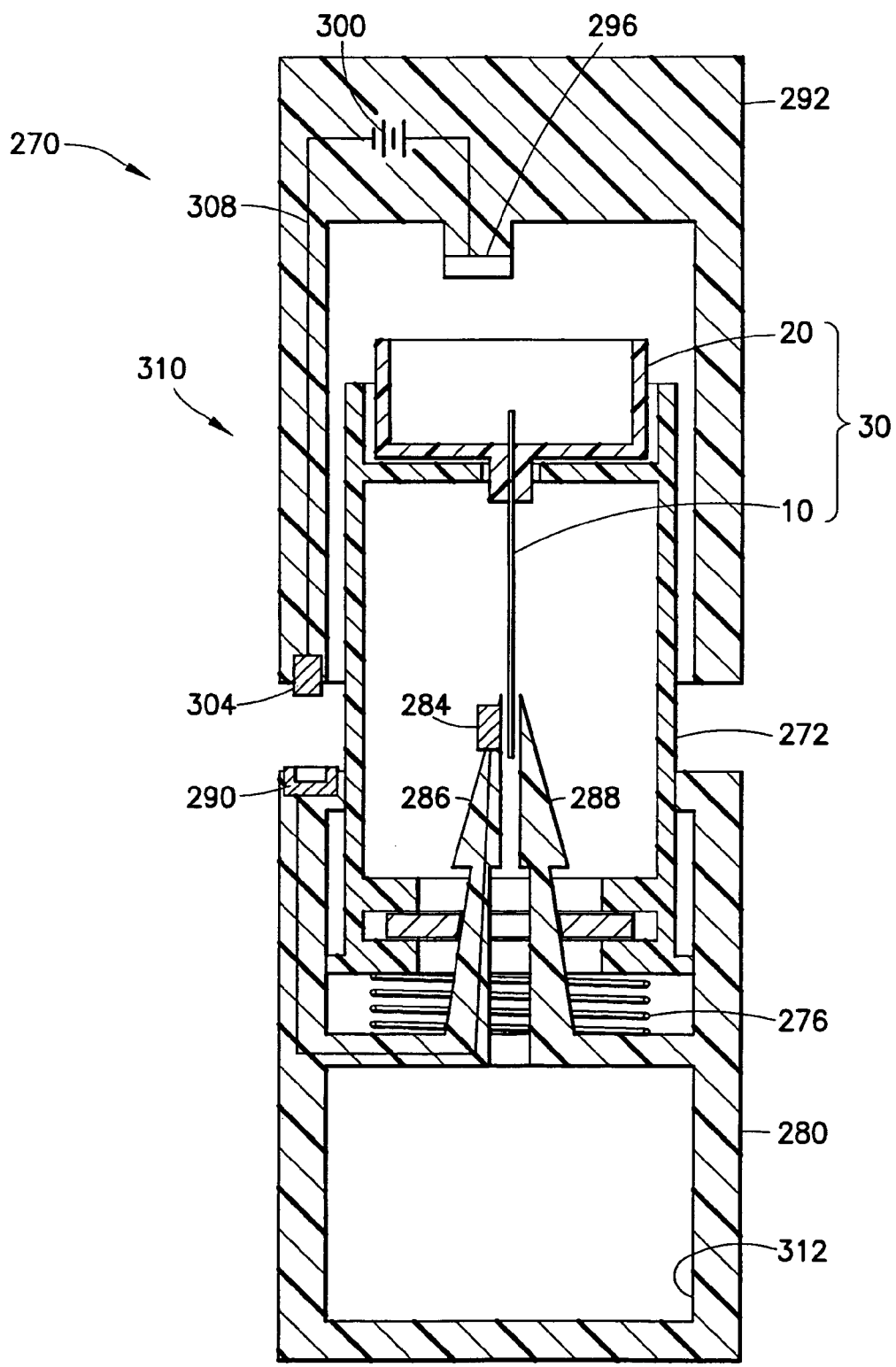
FIG. 6 is a cross-sectional schematic view of a needle removal and storage device in accordance with another embodiment of the present invention.

FIG. 6 is a cross-sectional schematic view of needle removal and storage device 270 in accordance with another embodiment of the present invention. In contrast to the previous embodiments, the device 270 is directed to completely removing a needle from a needle holder in which opposing ends of the needle are accessible. The receiving unit 272 and the biasing unit 276 are substantially similar to those illustrated in FIGS. 1 and 2. In contrast, however, the grasping unit 280 includes a first electrical contact 284 disposed on the first arm 286 and a first electrical coupler 290 disposed on an exterior surface of the grasping unit 280. In addition, the device 270 includes a cover or cap 292 that has a second electrical contact 296, a power source 300, and a second electrical coupler 304.

Figure 7:
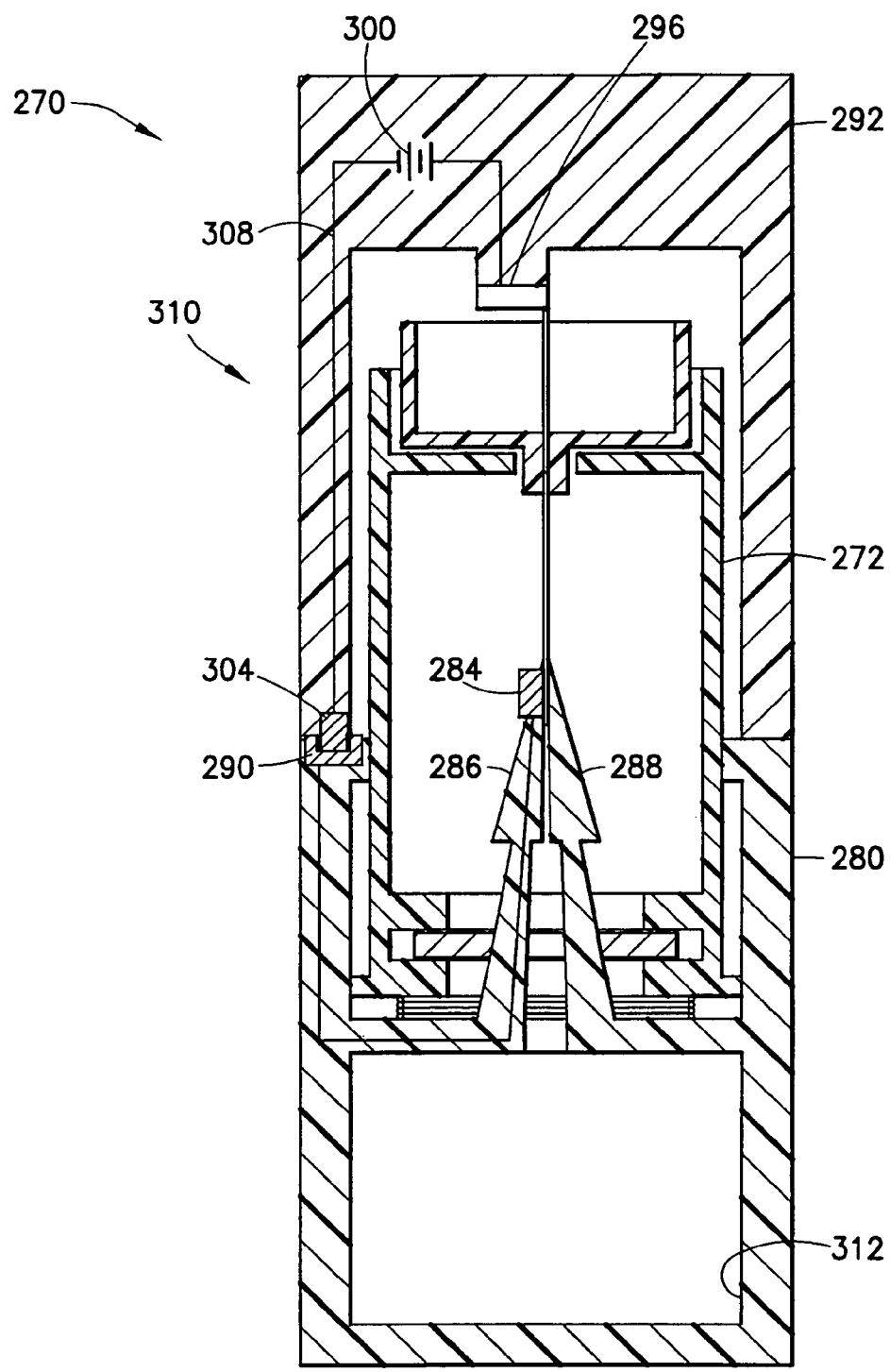
FIG. 7 is a cross-sectional schematic view of the device of FIG. 6 in operation.

In operation, as shown in FIG. 7, the user initially places the pen needle 30 in the receiving unit 272, and depresses the receiving unit 272 until the first and second arms 286 and 288 grasp the needle 10 and the first electrical contact 284 contacts a distal portion of the needle 10. The user then connects the cover 292 with the grasping unit 280. In doing so, the second electrical contact 296 contacts a proximal portion of the needle 10, and the second electrical coupler 304 couples with the first electrical coupler 291 thereby completing the electrical circuit 308. Separating means 310 includes the electrical circuit 308.

When electrical circuit 308 is complete, current passes through the needle 10. More particularly, in contrast to previously-described embodiments, current passes through the portion of needle 10 where the adhesive adheres the needle 10 to the needle holder 20 and/or where the material holds the needle 10 to the needle holder 20. This provides resistive heating directly at the joint between the needle 10 and the needle holder 20, whereas the previously-described embodiments rely on heat transfer axially along the needle to reach the joint. In other words, in the previously-described embodiments, electrical contacts or heating elements contact the needle in close proximity to the joint between the needle 10 and a needle holder 20, but even in the embodiments employing the electrical contacts, the current does not pass through the needle at the joint. Instead, the current passing through the portion of the needle (or the heating element) heats the needle and the heat transfers axially along the needle to the joint to melt, soften, or weaken the adhesive joint and/or material holding the needle 10 to the needle holder 20. The device 270 shown in FIGS. 6 and 7, however, provides quicker heating of the joint, and therefore, quicker needle removal.

According to one embodiment, the cover 292 is clear so that the user can see when the needle 10 is removed from the needle holder 20. According to another embodiment, the electrical circuit 308 includes an indicator light disposed on an exterior of the cover 292 that lights up when the electrical circuit 308 is complete, and goes out when the electrical circuit 308 is broken by first and second arms 286 and 288 moving apart and the needle 10 moving into the storage unit 312.

Figure 8:
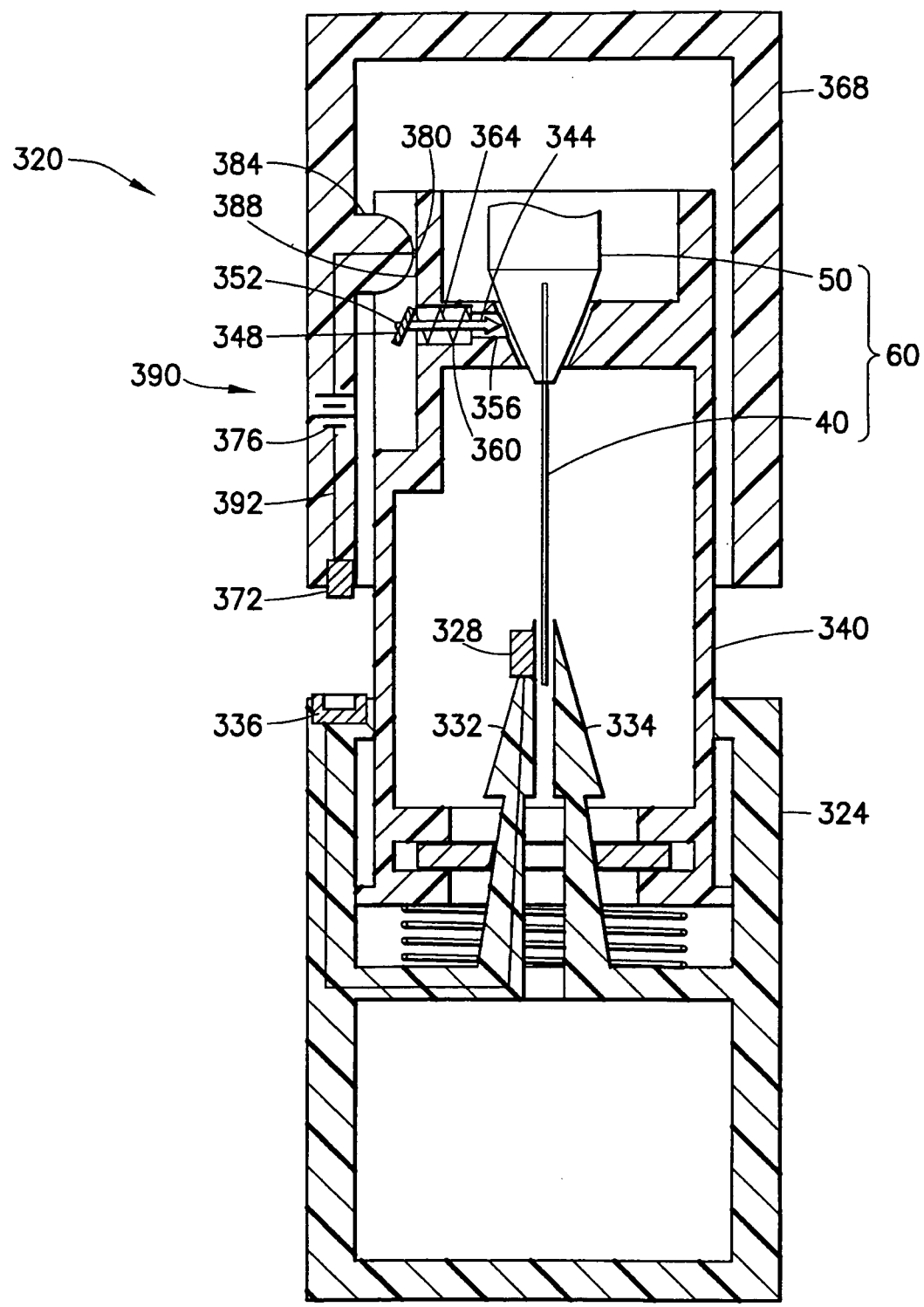
FIG. 8 is a cross-sectional schematic view of a needle removal and storage device in accordance with another embodiment of the present invention.

FIG. 8 is a cross-sectional schematic view of needle removal and storage device 320 in accordance with another embodiment of the present invention. Similar to the embodiments of FIGS. 6 and 7, in the device 320, the grasping unit 324 includes a first electrical contact 328 disposed on a first arm 332, and a first electrical coupler 336 disposed on an exterior of the grasping unit 324. The receiving unit 340, however, receives a needle holder 50 of a syringe needle 60. Additionally, the receiving unit 340 includes a second electrical contact 344 biased radially away from a central axis of the receiving unit 340. Thus, when the syringe needle 60 is received centrally in the receiving unit 340, the second electrical contact 344 is biased radially away from the syringe needle 60.

According to one embodiment, the second electrical contact 344 is a spike 344 for cutting through the needle holder 50 to contact needle 40. Further, the spike 344 includes a plate 348 with a third electrical contact 352 disposed on a radially outward side thereof. The spike 344 is radially movable within a radial channel 356 of the receiving unit 340, and the plate 348 is radially movable within a larger diameter radial channel 360 with a central axis coinciding with that of the radial channel 356. The plate 348 forms an angle with respect to the central axis of the radial channels 356 and 360. In addition, a second biasing unit 364 (for example, a spring 364) disposed within the larger diameter radial channel 360, biases the plate 340 (and thus, the spike 344) radially outward. The cover 368 includes a second electrical coupler 372 electrically connected to a power source 376, which is in turn electrically connected to a fourth electrical contact 380 disposed on an internal protrusion 384 of the cover 368.

Figure 9:
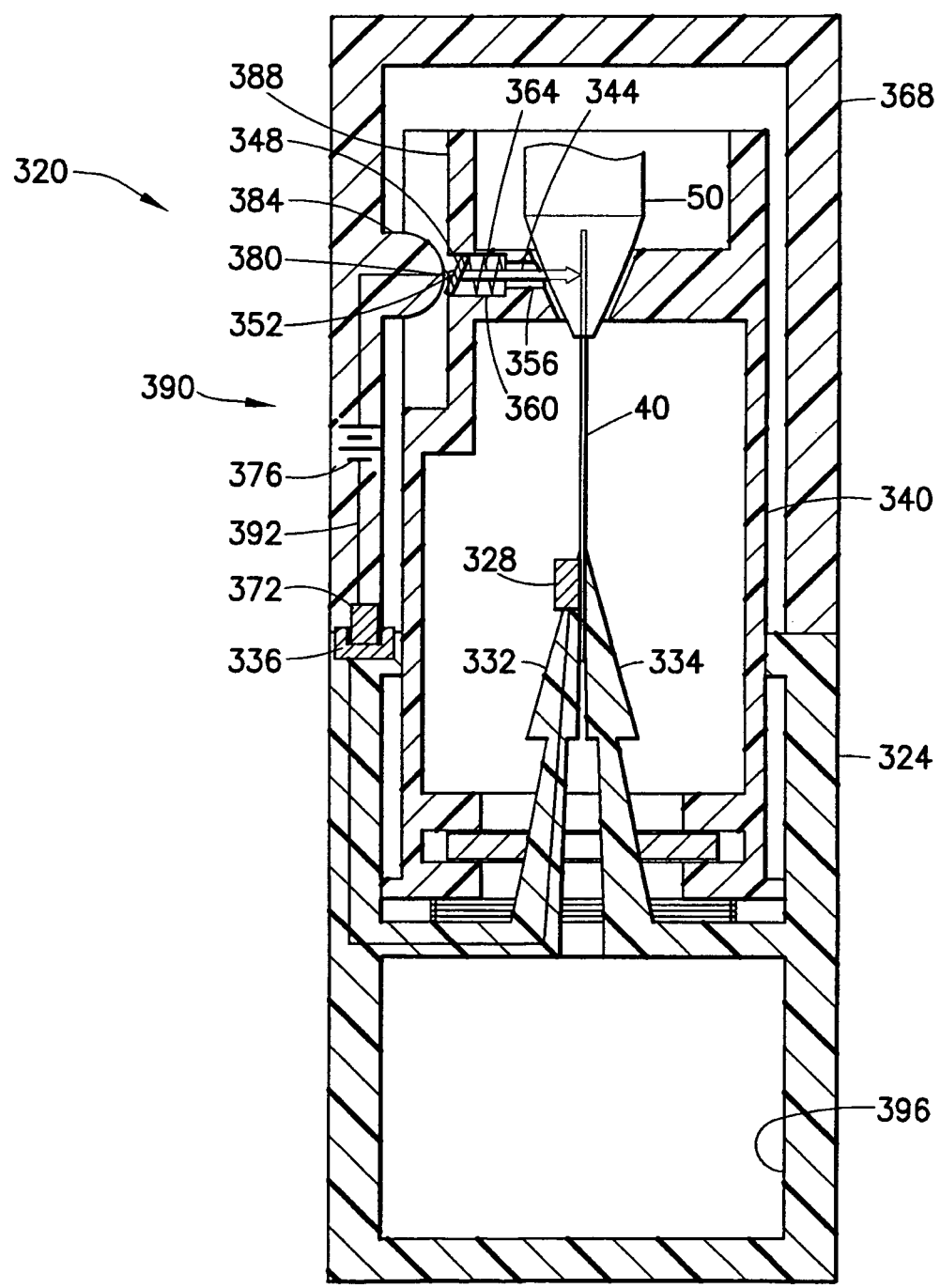
FIG. 9 is a cross-sectional schematic view of the device of FIG. 8 in operation.

In operation, as shown in FIG. 9, the user initially places the syringe needle 60 in the receiving unit 340, and depresses the receiving unit 340 until the first and second arms 332 and 334 grasp the needle 40 and the first electrical contact 328 contacts the needle 40. By then connecting the cover 368 with the grasping unit 324, the protrusion 384 passes through an axial channel or slot 388 connected with the radial channel 360 and drives the plate 348 and the spike 344 radially inward to cut the needle holder 50 and contact the needle 40, and the fourth electrical contact 380 contacts the third electrical contact 352. The spike 344 contacts the needle 40 where the adhesive adheres the needle 40 to the needle holder 50 and/or where the material holds the needle 40 to the needle holder 50. Moreover, the second electrical coupler 372 couples with the first electrical coupler 336, thereby completing the electrical circuit 392 through the needle 40. Thus, the device 320 also heats and thereby melts, softens, or weakens the adhesive and/or material at the joint between the needle 40 and the needle holder 50. Separating means 390 includes the electrical circuit 392.

Once the needle 40 moves into the storage unit 396, the user removes the cover 368, thereby breaking the electrical circuit 392. After removing the cover 368, the spike 344 and the plate 348 move radially outward under the force from the second biasing unit 364, to disengage the spike 344 from needle holder 50. At this point, the user can recycle or dispose of the needle holder 50 without the risk of needle-stick injury.

Figure 10:
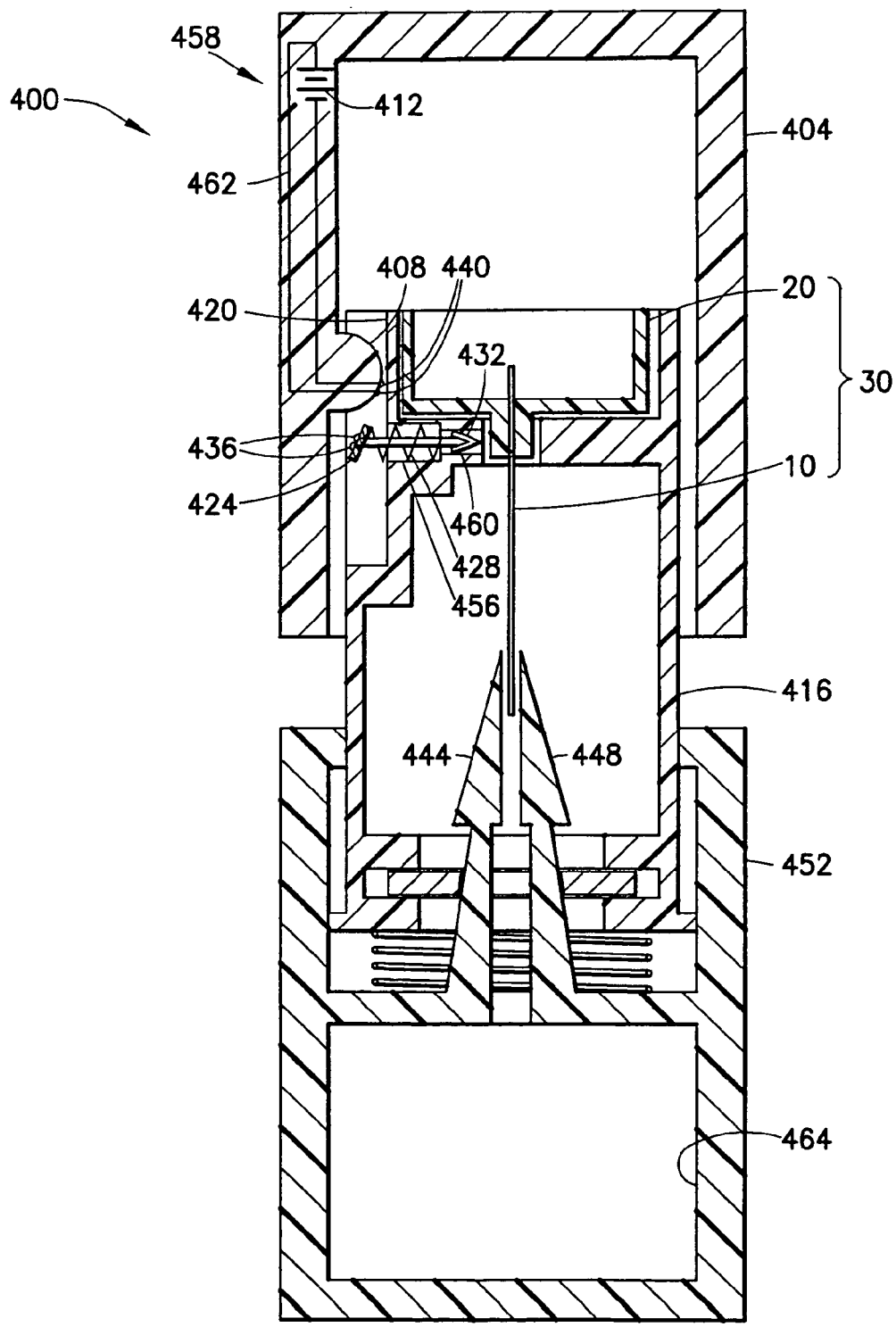
FIG. 10 is a cross-sectional schematic view of a needle removal and storage device in accordance with another embodiment of the present invention.
Figure 11:
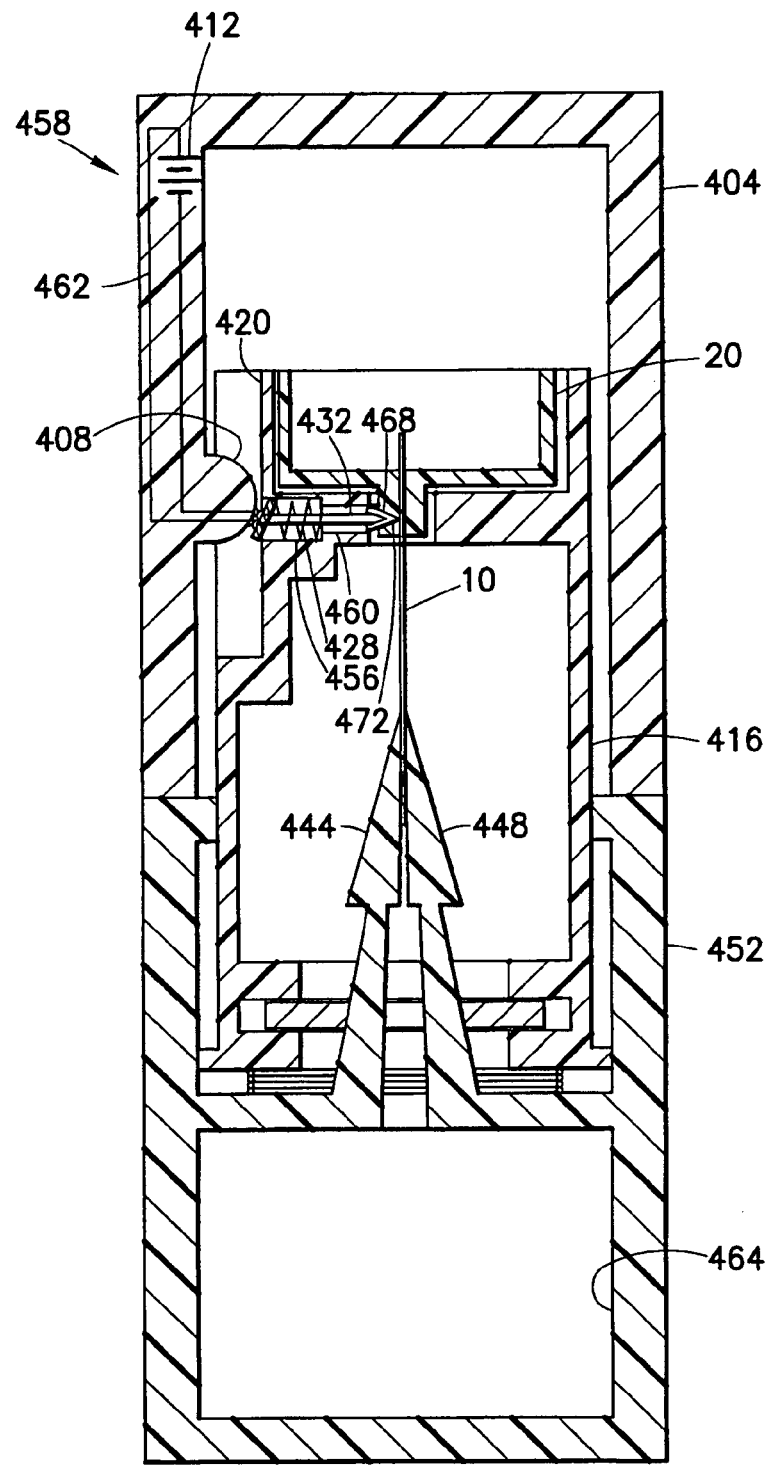
FIG. 11 is a cross-sectional schematic view of the device of FIG. 10 in operation.
Figure 12:
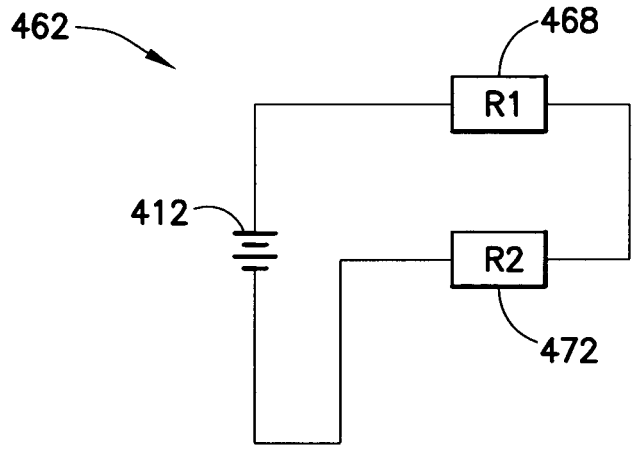
FIG. 12 is a schematic view of a circuit of the device of FIG. 10.

Like the cover 368, the cover 404 of another embodiment of needle removal and storage device 400 shown in FIGS. 10-12 includes a protrusion 408 and a power source 412 disposed on the cover 404. In addition, the receiving unit 416 includes an axial channel 420 in which the protrusion 408 travels and a plate 424 biased radially outward by a second biasing unit 428. But rather than a spike, the receiving unit 416 includes a heating element 432, for example, a nichrome wire 432, that burns or melts through the needle holder 20 to contact the needle 10 when connected to the power source 412.

To connect to the heating element 432 with the power source 412, the plate 424 has a pair of electrical contacts 436 electrically connected to the heating element 432. The protrusion 408 has a corresponding pair of electrical contacts 440 connected to the power source 412. In operation, the user places the pen needle 30 in the receiving unit 416 and depresses the receiving unit 416 until the first and second arms 444 and 448 grasp the needle 10. Subsequently, during connection of the cover 404 with the grasping unit 452, the protrusion 408 passes through the axial channel 424 and contacts the plate 424, connecting the respective electrical contacts 436 and 440 and driving the plate 424 radially inward in the radial channel 456. Driving the plate 424 through the radial channel 456 drives the heating element 432 through the radial channel 460 to burn or melt through the needle holder and contact the needle 10, to heat the needle 10 at the joint where the adhesive adheres the needle 10 to the needle holder 20 and/or where the material holds the needle 10 to the needle holder 20.

Once the needle 10 moves into the storage unit 464, the user removes the cover 404, thereby breaking the electrical circuit 462. After removing the cover 404, the heating element 432 and the plate 424 move radially outward under the force from the second biasing unit 428, to disengage the heating element 432 from needle holder 20. At this point, the user can recycle or dispose of the needle holder 20 without the risk of needle-stick injury. Separating means 458 includes electrical circuit 462.

As shown in FIG. 11, the heating element 432 includes a pair of resistive heating elements 468 and 472 having respective resistances R1 and R2. When connected, the electrical circuit 462 can be represented as shown in FIG. 12. In this state, the total resistance of electrical circuit 462 is R1+R2.

Figure 15:
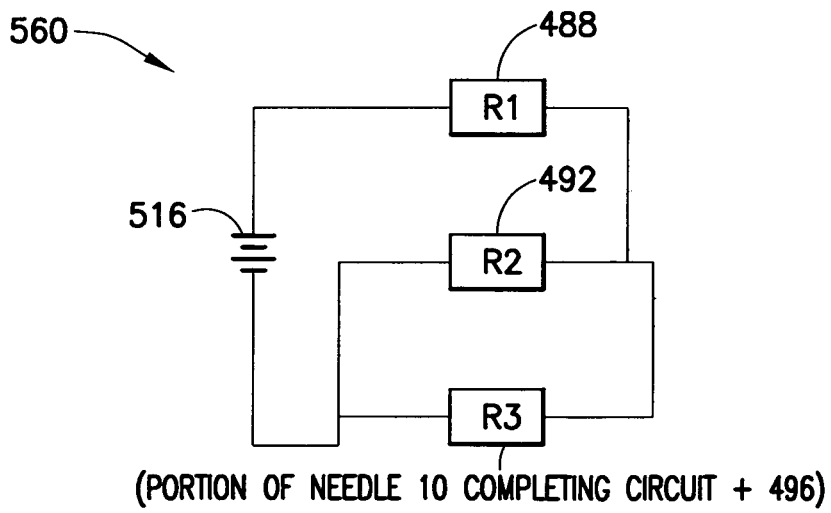
FIG. 15 is a schematic view of a circuit of the device of FIG. 13.
Figure 13:
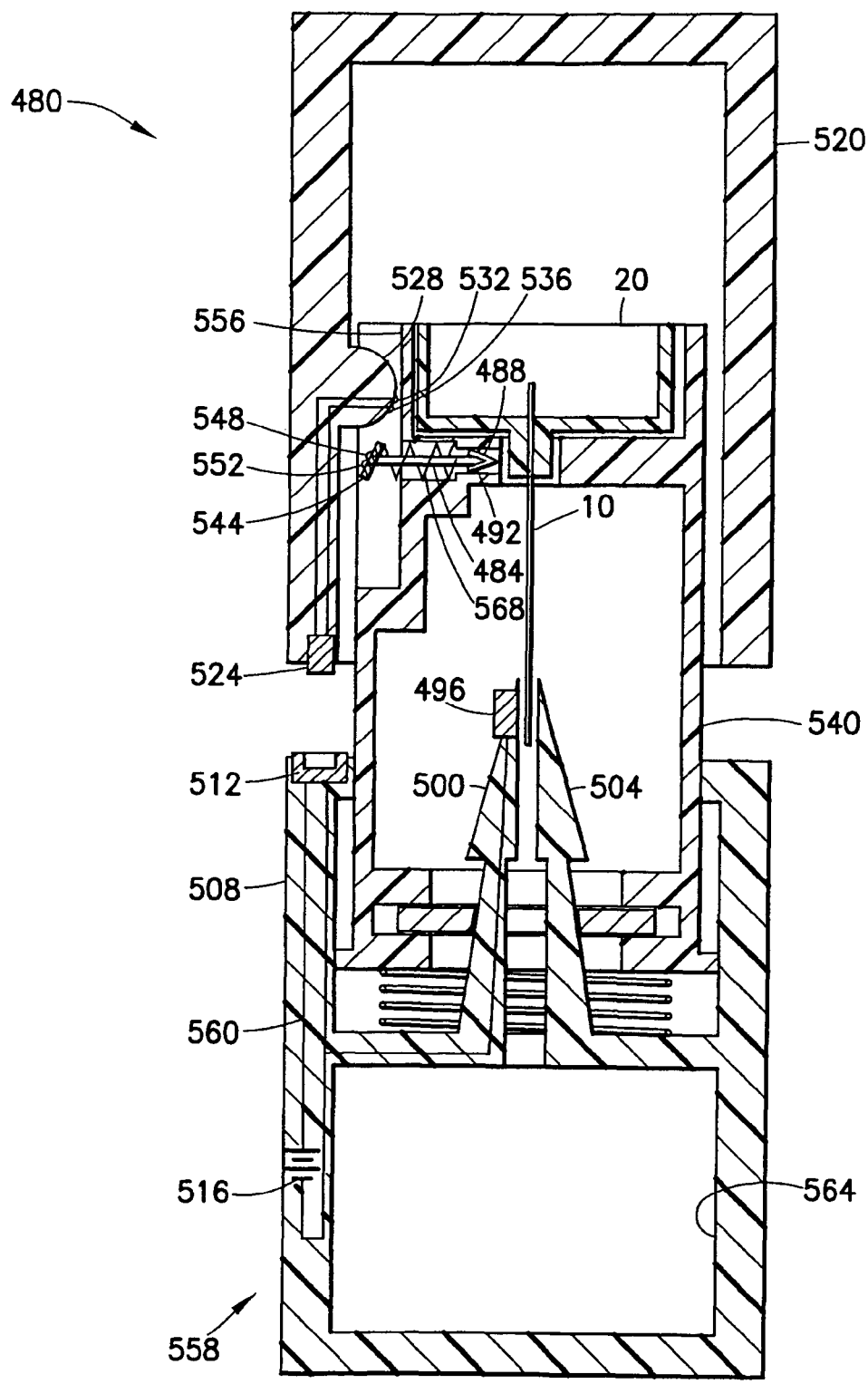
FIG. 13 is a cross-sectional schematic view of a needle removal and storage device in accordance with another embodiment of the present invention.
Figure 14:
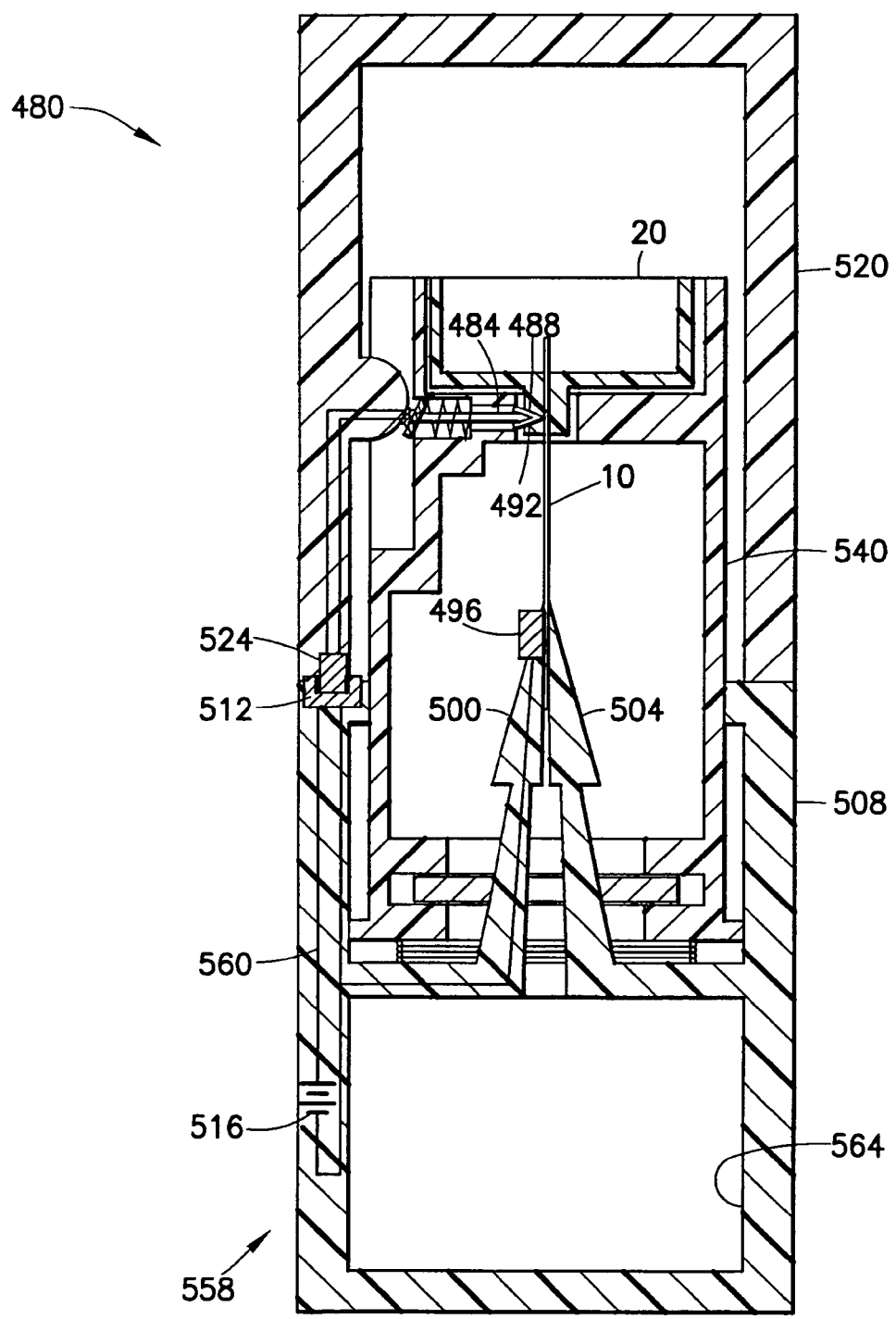
FIG. 14 is a cross-sectional schematic view of the device of FIG. 13 in operation.

Similar to the device 400, FIGS. 13-15 illustrate another embodiment of a needle removal and storage device 480. In addition to a heating element 484 including first and second resistive heating elements 488 and 492 the device 480 also has a first electrical contact 496 disposed on a first arm 500. Further, the grasping unit 508 includes a first electrical coupler 512 that is electrically connected to a power source 516 as well as the first electrical contact 496.

A cover 520 includes a second electrical coupler 524 and a protrusion 528 having second and third electrical contacts 532 and 536 disposed thereon. A receiving unit 540 includes a plate 544 is electrically connected to the heating element 484 and has fourth and fifth electrical contacts 548 in 552 disposed thereon for connection with the second and third electrical contacts 532 and 536, respectively.

In operation, as shown in FIG. 14, the user initially places the pen needle 30 in the receiving unit 540 and depresses the receiving unit 540 until the first and second arms 500 and 504 grasp the needle 10 and the first electrical contact 496 contacts the needle 10. By then connecting the cover 520 with the grasping unit 508, the protrusion 528 passes through the axial channel 556 in the receiving unit 540 and the second and third electrical contacts 532 and 536 on the protrusion 528 contact the fourth and fifth electrical contacts 548 and 552 on the plate 544, driving the plate 544 and the heating element 484 radially inward toward the needle 10. In addition, the first and second electrical couplers 512 and 524 couple together to complete the electrical circuit 560. Separating means 558 includes the electrical circuit 560.

In the state shown in FIG. 14, in which the heating element 488 has burned or melted through the needle holder 20 to contact the needle 10, current flows not only through the heating element 484, but through the needle 10 via the first electrical contact 496 disposed on the first arm 500. The current flowing through both paths of the electrical circuit 560 can be schematically represented as shown in FIG. 15. In this state, the total resistance of the electrical circuit 560 is R1+ ((R2*R3)/(R2+R3)). Thus, current flowing through both paths of the electrical circuit 560 creates a lower resistance, resulting in a higher power being dissipated, which results in rapid heating in the needle 10 and melting, softening, or weakening of the adhesive joint where the adhesive adheres the needle 10 to the needle holder 20 and/or where the material holds the needle 10 to the needle holder 20.

Once the needle 10 moves into the storage unit 564, the user removes the cover 520, thereby breaking the electrical circuit 560. After removing the cover 520 the heating element 484 and the plate 544 move radially outward under the force from the second biasing unit 568, to disengage the heating element 484 from needle holder 20. At this point, the user can recycle or dispose of the needle holder 20 without the risk of needle-stick injury.

Figure 16:
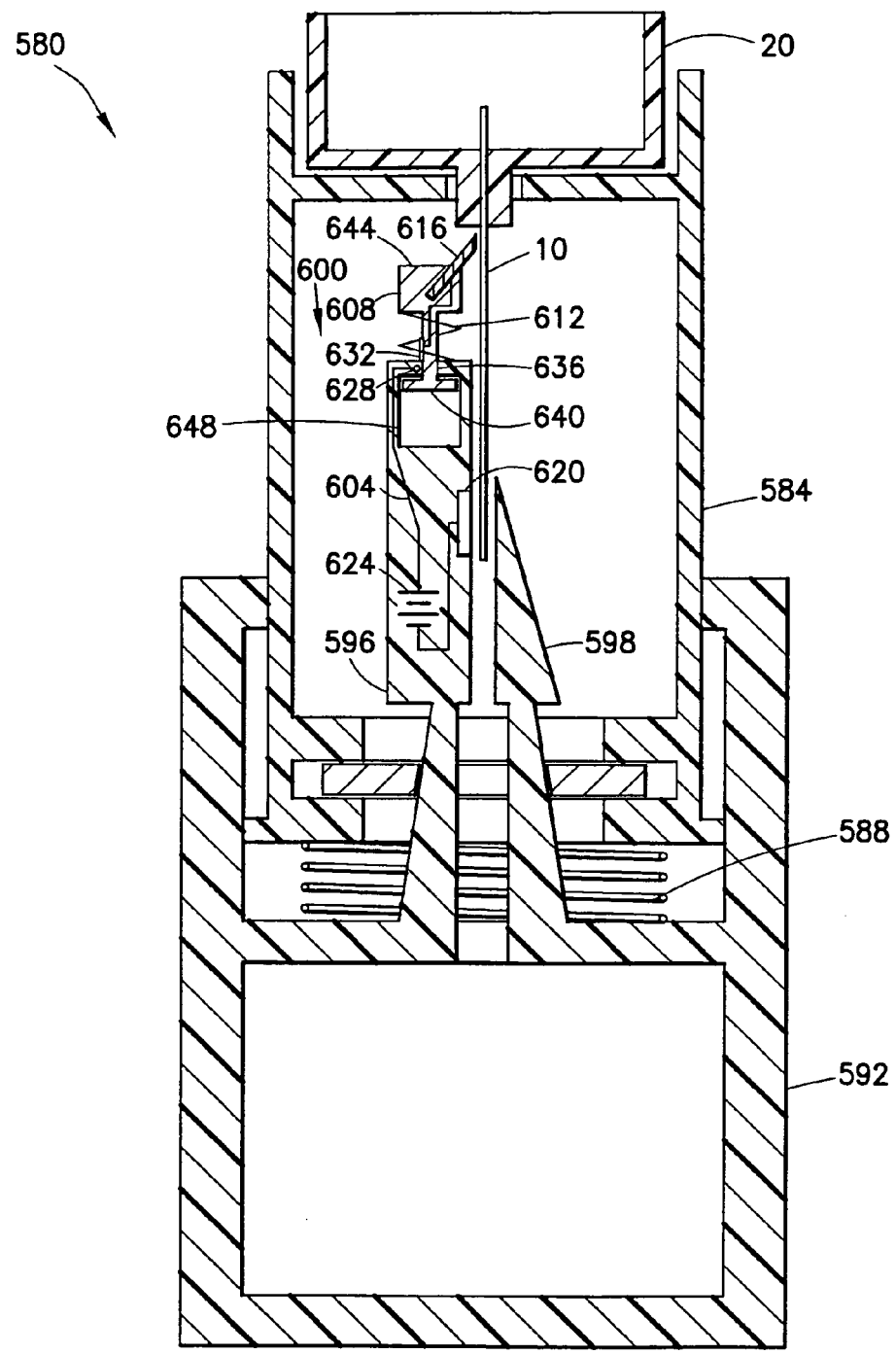
FIG. 16 is a cross-sectional schematic view of a needle removal and storage device in accordance with another embodiment of the present invention.
Figure 17:
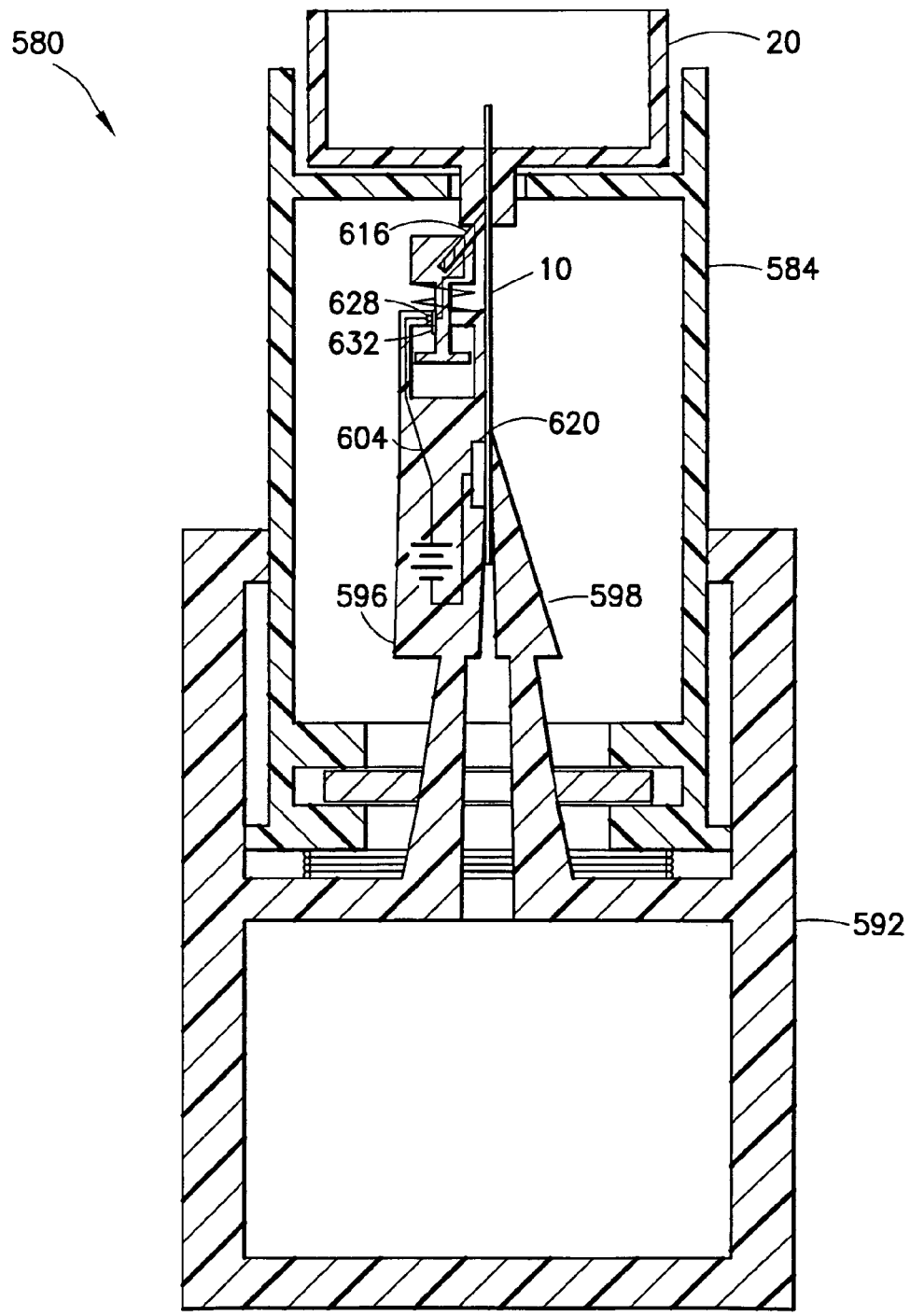
FIG. 17 is a cross-sectional schematic view of the device of FIG. 16 in operation.

FIGS. 16 and 17 are cross-sectional schematic views of a needle removal and storage device 580 in accordance with another embodiment of the present invention. The device 580 includes the receiving unit 584 receiving a pen needle 30, a first biasing unit 588, and grasping unit 592 including first and second arms 596 and 598. The device 580 also includes separating means 600 disposed on the first arm 596.

The separating means 600 includes an electrical circuit 604, a blade mount 608 displaceably disposed on the first arm 596 and biased upwardly (first direction) by a second biasing unit 612, and a blade 616 mounted on the blade mount 608. The electrical circuit 604 includes a first electrical contact 620, a power source 624, and a second electrical contact 628. The electrical circuit 604 also includes an electrical contact plate 632 electrically connected to the blade 616 and mounted on a neck portion 636 of the blade mount 608.

The blade mount 608 includes the neck portion 636 connecting a lower flange 640 and an upper mounting portion 644 on which the blade 616 mounts. The first arm 596 includes a pocket 648 for displaceably retaining the lower flange 640. In operation, as shown in FIG. 17, user initially places the pen needle 30 in the receiving unit 584 and then depresses the receiving unit 584 until the first and second arms 596 and 598 grasp the needle 10 and the first electrical contact 620 contacts the needle 10. This motion of the receiving unit 584 also brings the blade 616 into contact with the needle 10 and the needle holder 20, thereby depressing the blade mount 608 and sliding the electrical contact plate 632 into contact with the second electrical contact 628 to complete the electrical circuit 604 through the needle 10.

In addition to cutting the needle holder 20, by being part of the electrical circuit 604, the blade 616 also acts as a resistive heating element to melt or burn the needle holder 20. Thus, the cutting and melting or burning by the blade 616, in combination with heating of the needle 10 due to the current flow therethrough, provides for quick separation of the needle 10 from the needle holder 20.

Although certain embodiments of FIGS. 1-17 are directed to removing a needle from a pen needle holder, one skilled in the art will appreciate that, generally, the concepts can also be implemented for syringes. Conversely, one skilled in the art will appreciate that those embodiments directed to removing a needle from a syringe needle holder can also be implemented for pen needles.

Figure 18:
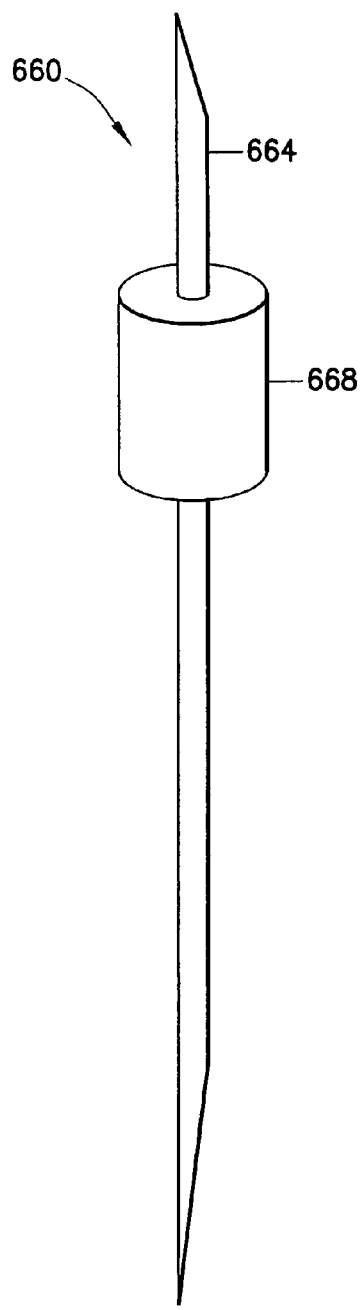
FIG. 18 is a perspective view of a bead-needle assembly in accordance with an embodiment of the present invention.

FIG. 18 is a perspective view of a bead-needle assembly 660 for a pen injection device in accordance with an embodiment of the present invention. The bead-needle assembly 660 includes a needle 664 and a bead 668. According to one embodiment, the needle 664 is a standard pen needle cannula and the bead 668 is made of a soft rubber-like material, for example, a liquid silicone rubber (LSR) or thermo-plastic elastomer (TPE). According to one embodiment, the bead 668 is molded onto the needle 664. The reason for the bead 668 being made of a rubber-like material is to easily remove/cut away the bead 668 from the needle 664 after use.

Figure 19:
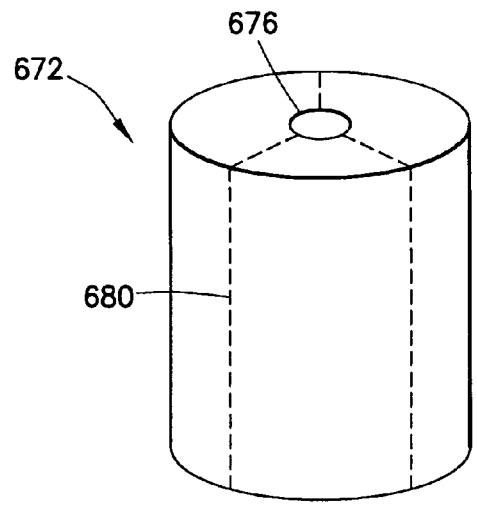
FIGS. 19-21 are perspective views of alternative beads.
Figure 20:
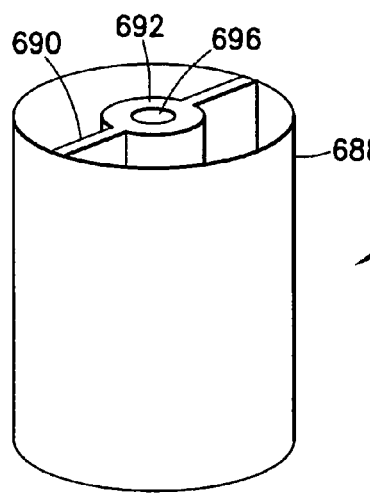
Figure 21:
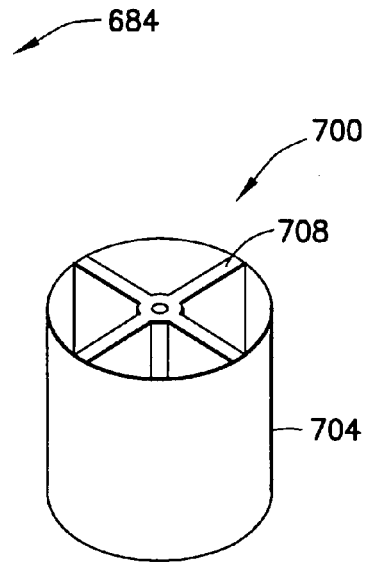

FIGS. 19-21 illustrate alternative beads that could be employed with the needle 664. In FIG. 19, the bead 672 is substantially cylindrical and has a central bore 676 therethrough for accommodating the needle 664. Additionally, the bead 672 is perforated 680. The bead 684 in FIG. 20 includes an outer cylinder 688 connected by radial spoke arms 690 with an inner cylinder 692 having a central bore 696 therethrough for accommodating the needle 664. As shown in FIG. 21, the bead 700 includes a cylinder 704 with an internally extending radial spoke arms 708 that meet centrally within the cylinder 704 to accommodate the needle 664.

Figure 22:
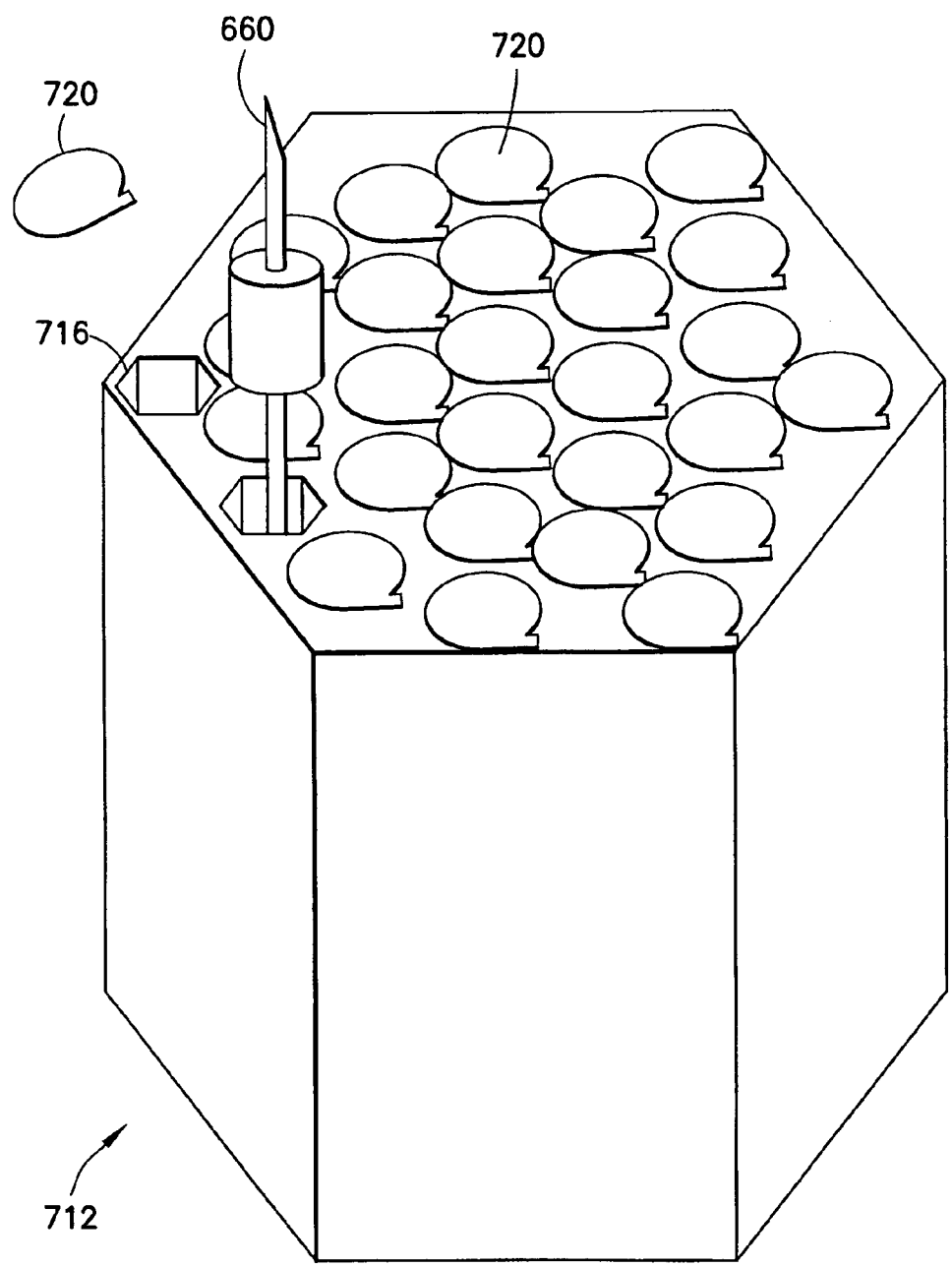
FIG. 22 is a carrier for the bead-needle assembly of FIG. 18.

FIG. 22 is a perspective view of a carrier 712 for a plurality of bead-needle assemblies 660. As shown in FIG. 22, the bead-needle assemblies 660 can be packaged in a honeycomb-like matrix package 712. This type of packaging is efficient in terms of packing density and in terms of the amount of plastic required to manufacture the carrier 712. After insertion of a bead-needle assembly 660 into each of the cells 716 of the carrier 712, removable sealing tabs or labels 720 secure the cells 716 and maintain the sterility of the bead-needle assemblies 660 prior to use.

Figures 23, 24:
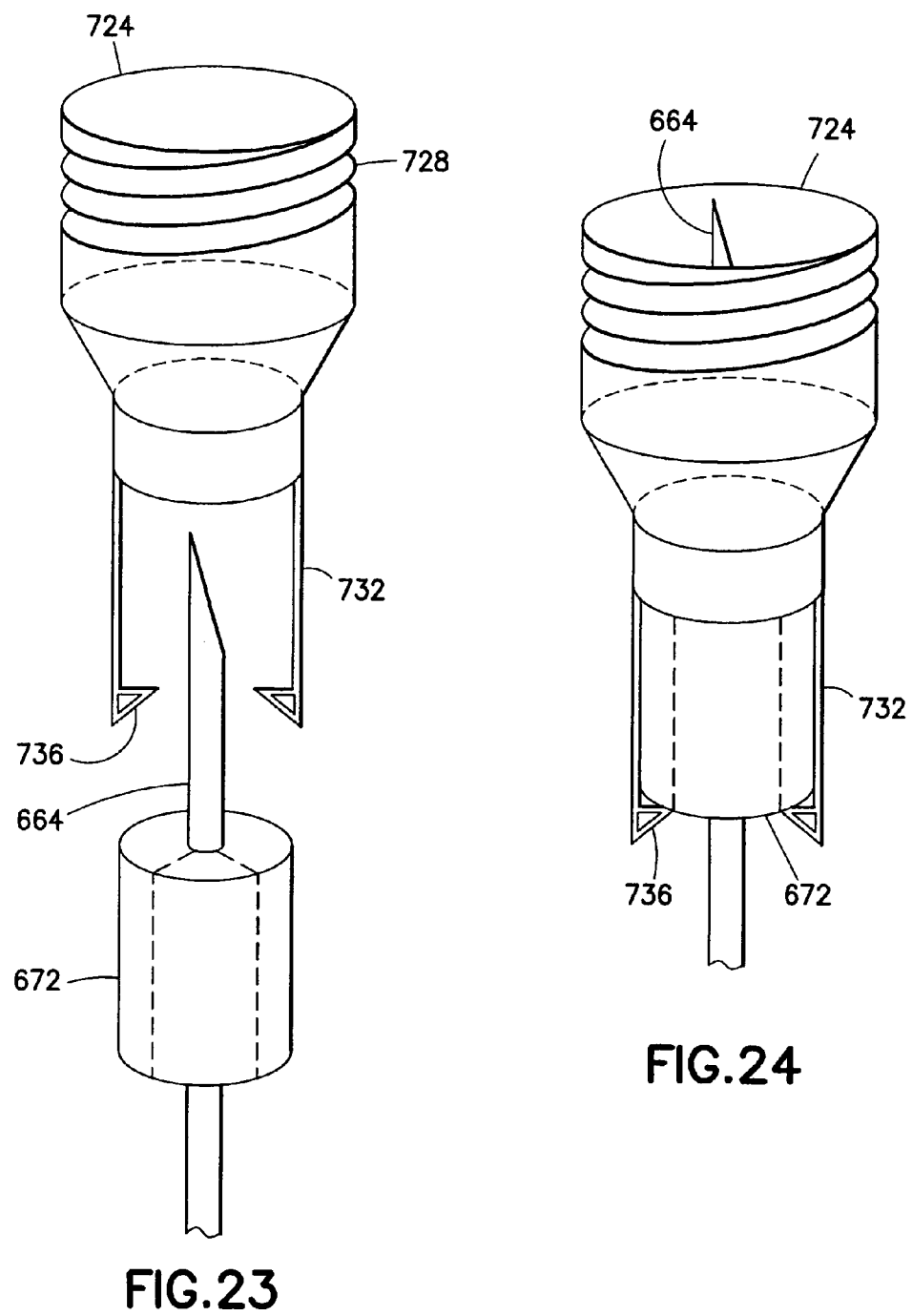
FIGS. 23 and 24 are partial perspective views illustrating connection of an injection pen adapter and the bead-needle assembly of FIG. 18.

To connect the bead-needle assembly 660 with a pen injection device, as shown in FIGS. 23 and 24, an adapter 724 threaded for connection with a pen injection device selectively secures the bead needle assembly 660. The adapter 724 includes a threaded portion 728 for connection with a threaded end of a pen injection device. Additionally, the adapter 724 includes a plurality of cantilevered arms 732 with hooks 736 disposed of free ends thereof. To mount the bead-needle assembly 660 in the adapter 724 the user first threads the adapter onto the pen injection device. In FIG. 24, however, the injection device is omitted for clarity. Subsequently, the user axially aligns the adapter 724 and bead-needle assembly 660 and presses the adapter 724 over the bead-assembly. Canted faces of the hooks 736 contact the bead 672 and displace the ends of the cantilevered arms 732 outwardly, permitting the cantilevered arms to slide over the bead 672. Once the hooks 736 pass a distal end of the bead 672, as shown in FIG. 24, the cantilevered arms 732 snap back to their original position and the hooks 736 secure the bead-needle assembly 660 within the adapter 724.

Figures 25, 26:
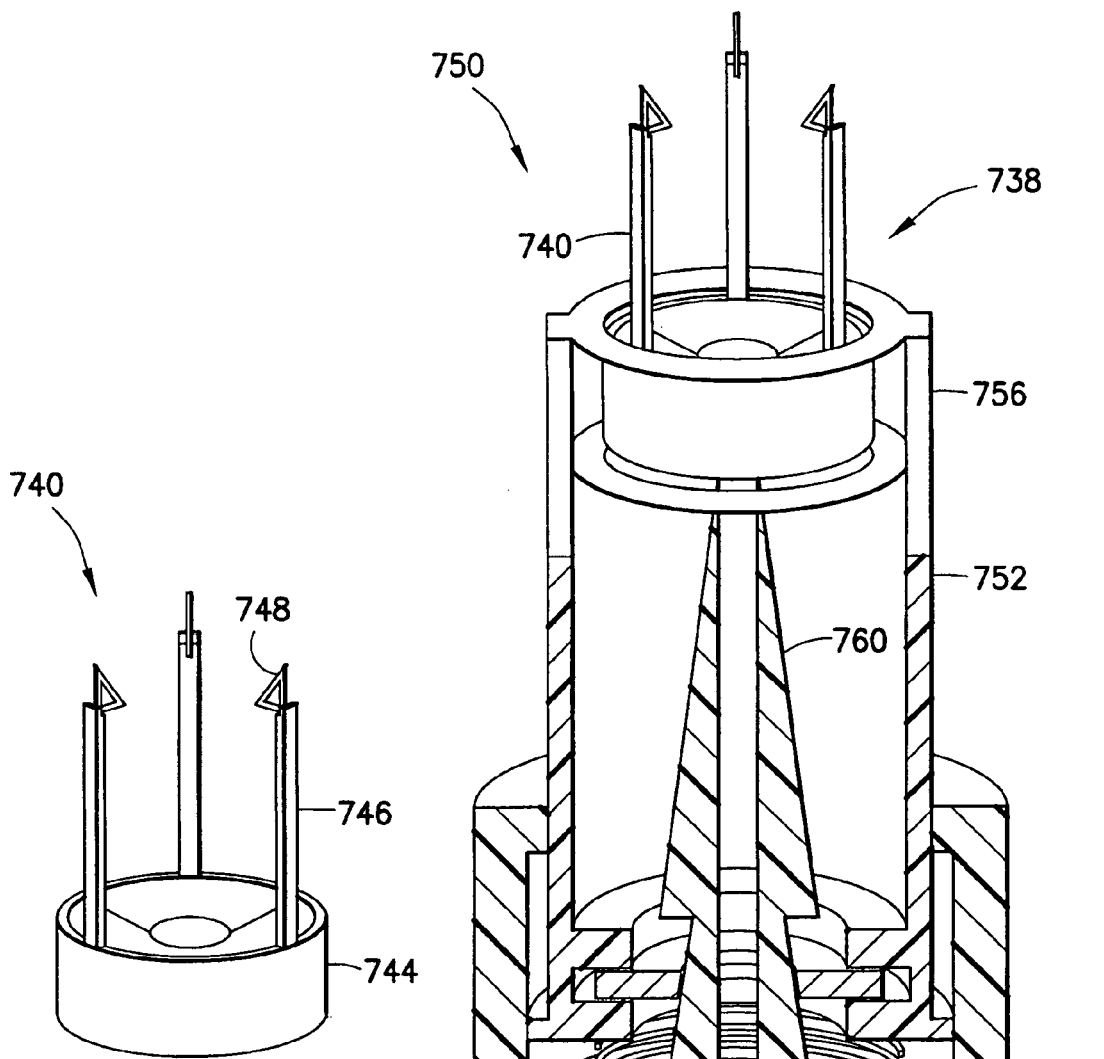
FIG. 25 is a partial perspective view of a cutting unit.
FIG. 26 is a partial perspective view of a needle removal and storage device in accordance with another embodiment of the present invention.

FIG. 25 is a partial perspective view of a cutting unit 740 and FIG. 26 is a partial perspective view of a needle removal and storage device 750 employing the cutting unit 740 in accordance with another embodiment of the present invention. Separating means 738 includes the cutting unit 740. The cutting unit 740 includes a base 744 with a plurality of cantilevered arms 746, each having a blade 748 disposed at free end thereof. The cantilevered arms 746 are circumferentially spaced around the base 744 to accommodate the cantilevered arms 732 of the adapter 724 therebetween. As shown in FIG. 26, a proximal end of a receiving unit 752 includes a cage 756 for securely holding the cutting unit 740. According to one embodiment, the cage 756 is configured to selectively hold the cutting unit 740, so that the cutting unit 740 can be replaced when the blades 748 become dull.

In operation, the user aligns the cantilevered arms 732 of the adapter 724 between the cantilevered arms 746 of the cutting unit 740 and presses the pen injection device downward (second direction), thereby displacing the receiving unit 752 downward until the arms 760 of the grasping unit 764 grasp the needle 664. During this motion, the blades 748 of the cutting unit 740 slice the bead 672 and separate the bead 672 from the needle 664. As the user withdraws the pen injection device, a biasing unit 768 displaces the receiving unit 752 upward (first direction) permitting the arms 760 to move back to their initial position and permitting the needle 664 to fall into the storage unit 772. At this point, the user can remove the cut pieces of the bead 672 from the adapter 724 and recycle or dispose of the cut pieces without the risk of needle-stick injury.

Figure 28:
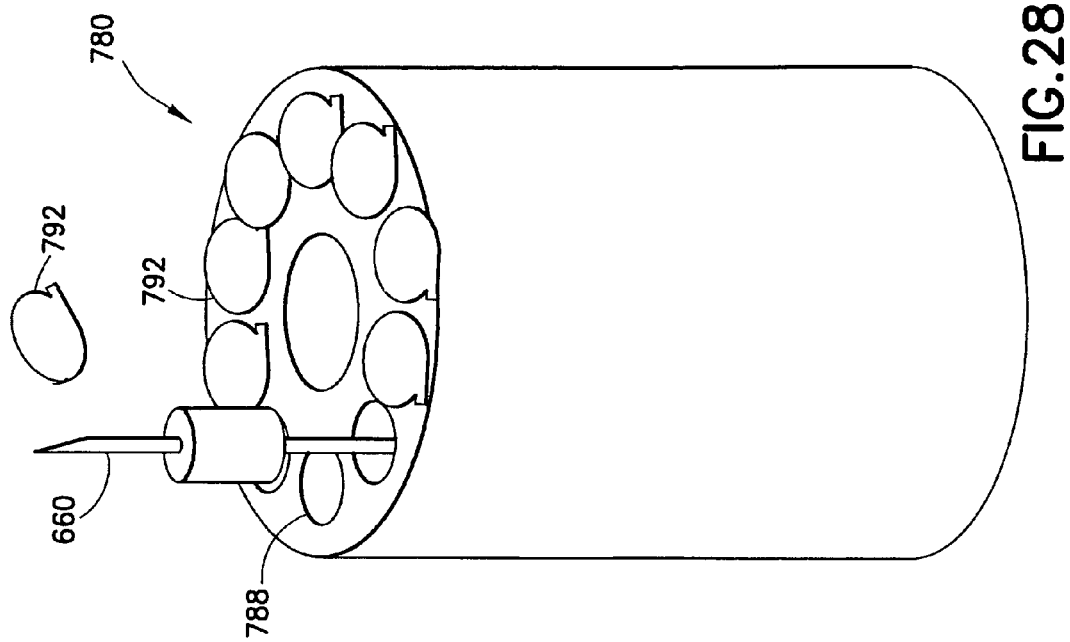
FIGS. 27 and 28 are perspective views of opposing ends of a carrier and needle removal and storage device in accordance with another embodiment of the present invention.
Figure 27:
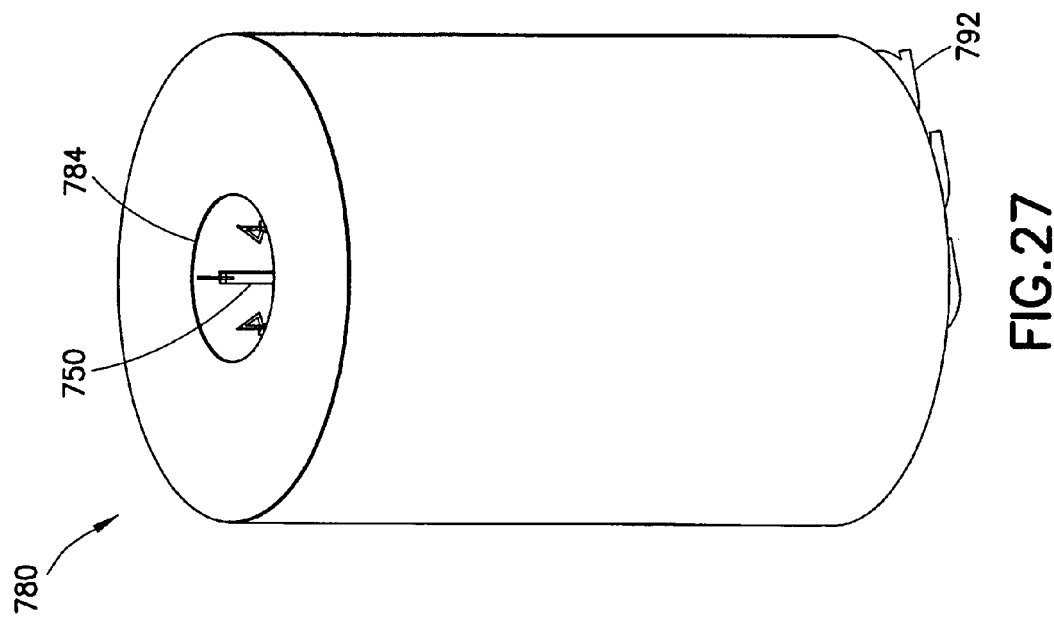

FIGS. 27 and 28 are perspective views of opposing ends of a carrier and needle removal and storage device 780 in accordance with another embodiment of the present invention. As shown in FIG. 27, the device 780 has a central opening 784 in a first end thereof providing access to a needle removal and storage device, such as the device 750. The opposing end of the device 780, as shown in FIG. 28, includes cells 788 for storing bead-needle assemblies 660. Removable sealing tabs or labels 792 secure the cells 788 and maintain the sterility of the bead-needle assemblies 660 prior to use.

Figure 29:
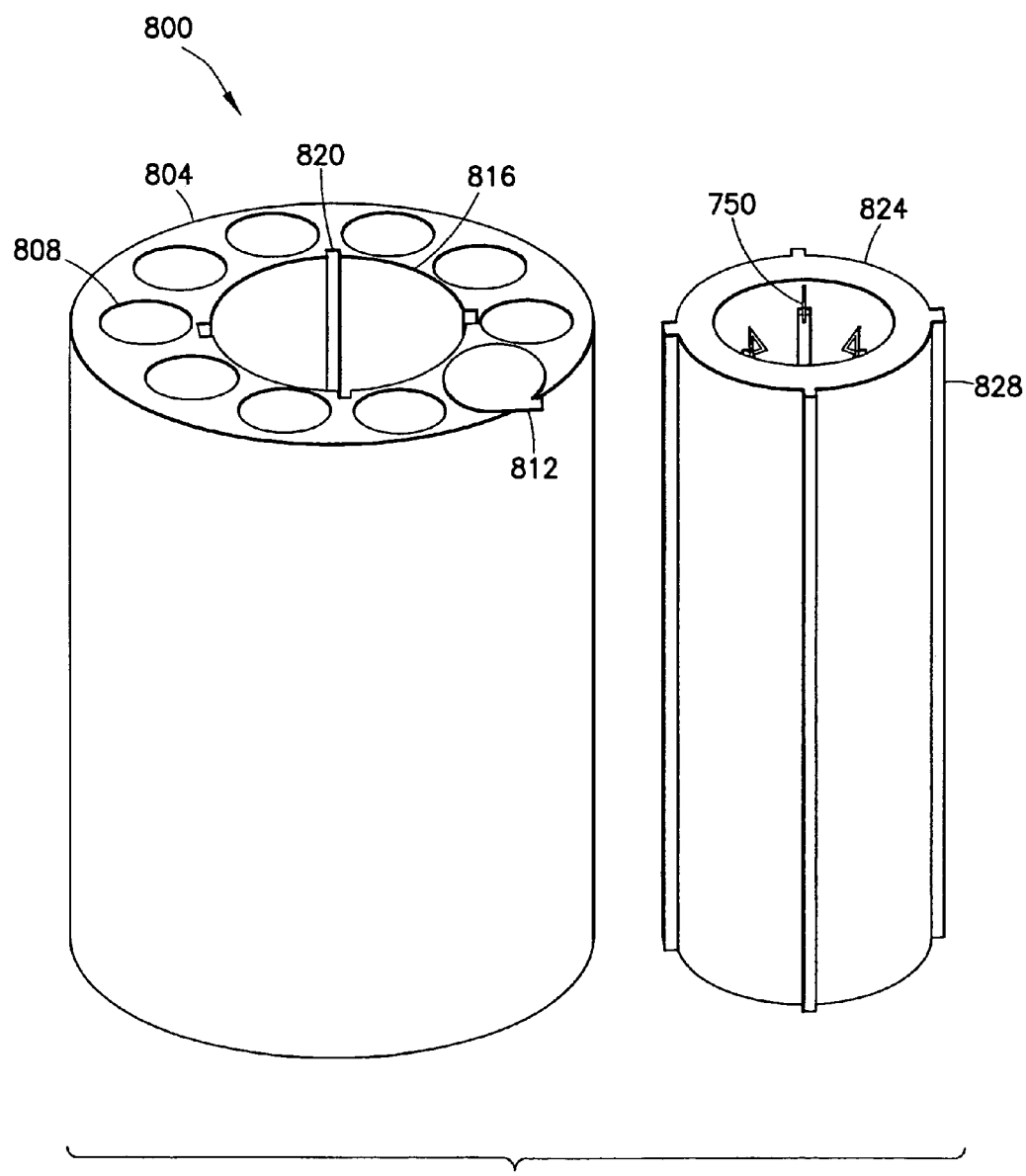
FIG. 29 is a perspective view of a carrier and needle removal and storage device in accordance with another embodiment of the present invention.

FIG. 29 is a perspective view of a carrier and needle removal and storage device 800 in accordance with another embodiment of the present invention. The device 800 includes a carrier 804 having cells 808 for storing bead-needle assemblies 660. Removable sealing tabs or labels 812 secure the cells 808 and maintain sterility of the bead-needle assemblies 660 prior to use. Additionally, the carrier 804 has a central opening 816 with grooves 820 extending radially outward therefrom.

According to one embodiment, the storage unit, such as storage unit 772 of the device 750 can hold the significant number of separated needles 664. More specifically, the storage unit 772 can hold more needles 664 than the carrier 804 can carry. Accordingly, the device 800 includes a separable needle removal and storage device holder 824 that has a needle removal and storage device, such as device 750 disposed therein. The holder 824 has axial fins 828 corresponding to the grooves 820 to selectively secure the holder 824 within the central opening 816 of the carrier 804. After using all of the bead-needle assemblies 660 in the carrier 804, the user can remove the holder 824 from the carrier 804 and install the holder 824 into a new carrier 804 with unused bead-needle assemblies 660.

Although the embodiments of FIGS. 18-29 are directed to a fundamentally different needle assembly for pen injection devices, one skilled in the art will appreciate that the concept can also be implemented for syringes.

Figure 30:
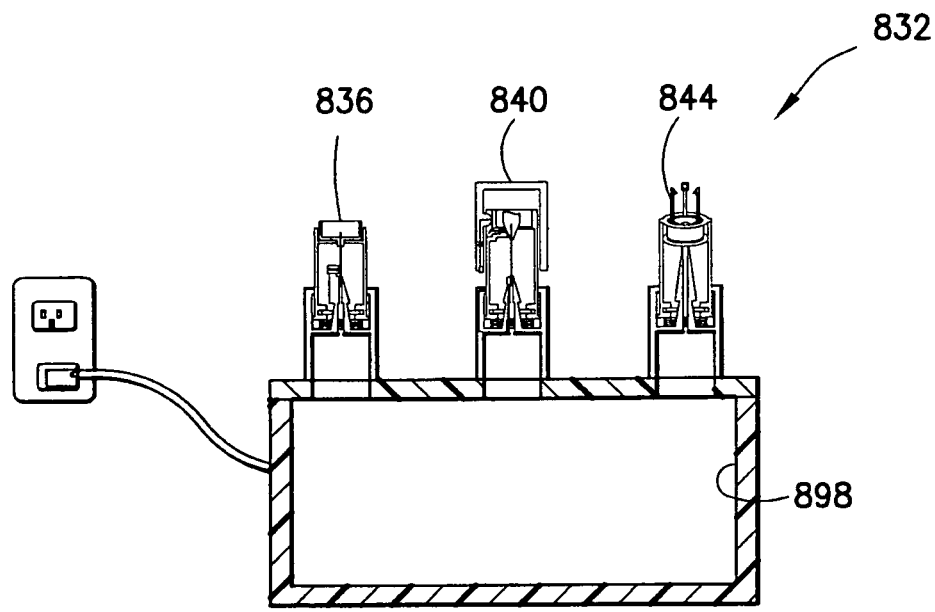
FIG. 30 is a cross-sectional schematic view of a sharps container with needle removal and storage devices in accordance with embodiments of the present invention disposed thereon.

FIG. 30 is a cross-sectional schematic view of a sharps container or box 832 with needle removal and storage devices in accordance with embodiments of the present invention disposed thereon. For example, as shown in FIG. 30, the sharps box 832 includes a pen needle device 836, a syringe needle device 840, and a bead-needle device 844. Further, the sharps box 832 includes a common storage unit 848 that stores needles from all three devices 836, 840, and 844. This box-like needle remover and containment device may be utilized, for example, in ambulances or stationary locations, such as clinics or hospitals.

Figure 31:
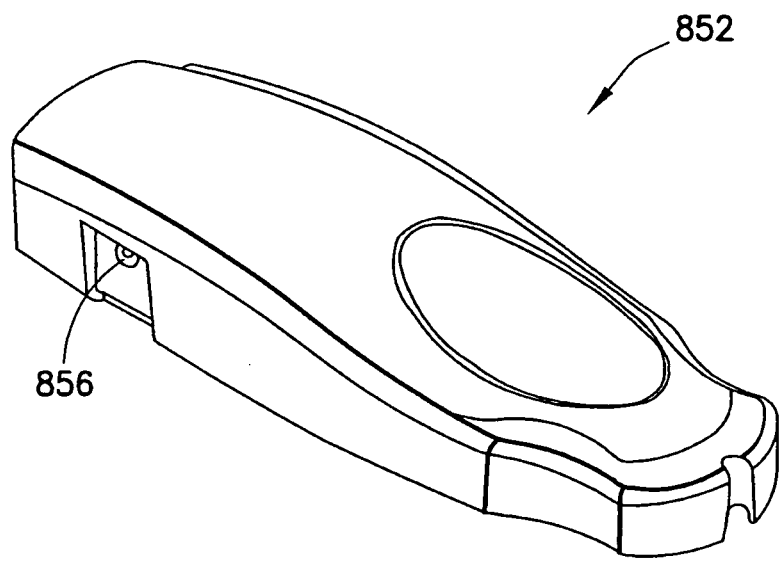
FIG. 31 is a perspective view of a case including a needle removal and storage device in accordance with an embodiment of the present invention.

FIG. 31 is a perspective view of a case 852 having a needle removal and storage device in accordance with an embodiment of the present invention disposed therein. A user inserts the needle into a port 856 on a side of the case 852 to access the needle removal and storage device. The case 852 provides a slim, portable unit for the convenience of a user.

Figure 32:
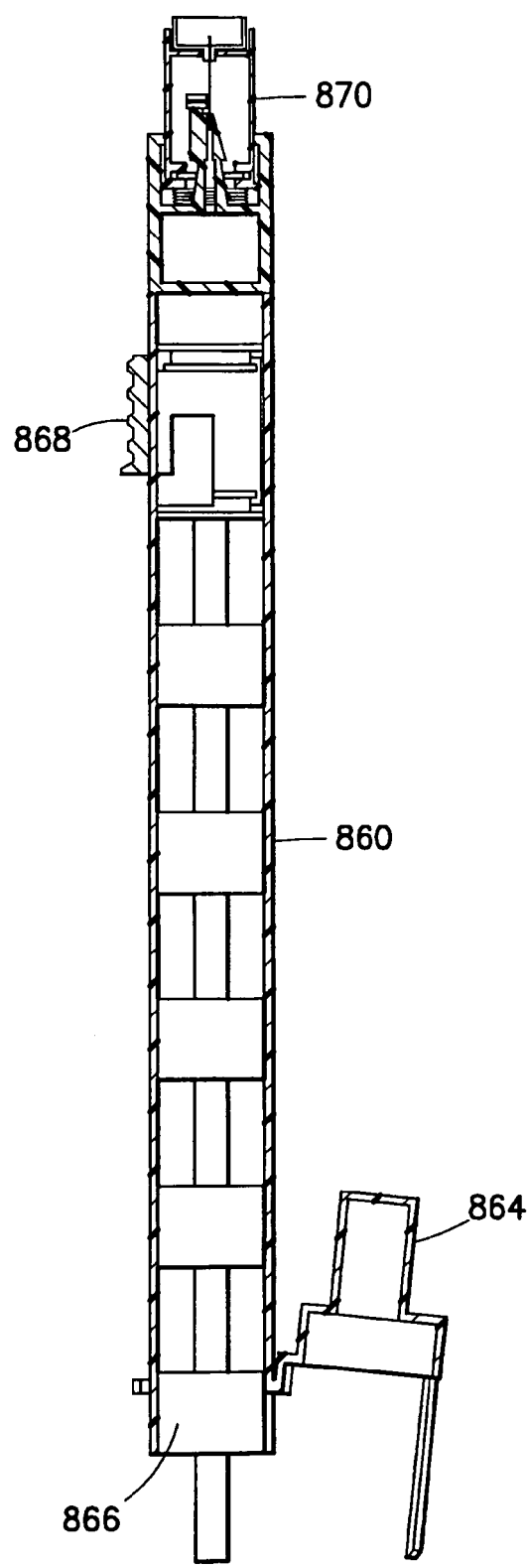
FIG. 32 is a perspective view of a pen needle dispenser with a needle removal and storage device in accordance with an embodiment of the present invention disposed thereon.

FIG. 32 is a perspective view of a pen needle dispenser 860 with a needle removal and storage device 870 in accordance with an embodiment of the present invention disposed thereon. The dispenser 860 includes a cover 864 at a first end, a plurality of pen needles 866 disposed therein, and an advancing unit 868 for advancing the pen needles 866 toward the first end. The device 870 is disposed at a second end of the dispenser 860 for the convenience of a user.

FIG. 33 is a perspective view of another pen needle dispenser 900 with a needle removal and storage device 904 in accordance with an embodiment of the present invention disposed thereon. According to one embodiment, the dispenser 900 has a short cylindrical body 908 and the device 904 is disposed centrally within the body 908. One skilled in the art will appreciate, however, that other shapes and other positions for the device 904 may be employed without departing from the scope of the present invention. The dispenser 900 has a plurality of cells 912 for holding a corresponding plurality of pen needles 30. Each cell 912 has a lid or cover 916 for sealing the cell 912.

According to one embodiment, a user opens a lid 916 to expose a pen needle 30 within a cell or cavity 912. The pen needle 30 may be encased in a plastic case with a sterile paper cover 920 or may have a sterile paper cover 920 attached directly thereto. The user removes the pen needle 30 from the body 908 (for example, by turning over the dispenser 900), removes the sterile cover 920, and attaches the pen needle 30 to a pen injection device. Subsequent to injection, the user presses the pen injection device with the needle 30 attached thereto into the device 904, which removes the needle 10 from the needle holder 20. The user can then recycle or dispose of the needle holder 20 without risk of needle-stick injury. Alternatively, the user can replace the needle holder 20 in the cell 912 and close the lid 916 to recycle or dispose of the needle holder 20 at a more convenient time. In such an embodiment, the user can restock the cells 912 with unused pen needles 30.

FIG. 34 is a perspective view of another pen needle dispenser 950 with a needle removal and storage device 952 in accordance with an embodiment of the present invention disposed thereon. According to one embodiment, the dispenser 950 includes a pen needle dispenser as disclosed in U.S. Pat. No. 5,873,462 to Nguyen et al., hereby incorporated by reference in its entirety. Similar to the device 900, the dispenser 950 has a short cylindrical body 956 and the device 952 is disposed centrally within the body 956. One skilled in the art will appreciate, however, that other shapes and other positions for the device 952 may be employed without departing from the scope of the present invention. The dispenser 950 has a plurality of cells or cavities 960 for holding a corresponding plurality of pen needles 30.

In contrast to the dispenser 900, however, rather than lids for each cell 960, the dispenser 950 includes a rotatable cover 964 (shown disconnected from the body 956 in FIG. 34 for clarity). The cover 964 includes a central opening 966 for accessing the device 952 and a selecting opening or slot 968 to selectively align with a cell 960 to dispense a pen needle 30 therefrom. According to one embodiment, the body 956 also has a blank space 972 for alignment with the selecting opening 968 during transport, to maintain the pen needles 30 within the dispenser 950.

In use, a user rotates the cover 964 to align the selecting opening 968 with a selected one of the cells 960 and removes a pen needle 30 (for example, by turning over the dispenser 950), removes the sterile cover 976, and attaches the pen needle 30 to a pen injection device. Subsequent to injection, the user presses the pen injection device with the needle 30 attached thereto into the device 952, which removes the needle 10 from the needle holder 20. The user can then recycle or dispose of the needle holder 20 without risk of needle-stick injury.

According to another embodiment, the user can replace the needle holder 20 in the cell 960 and rotate the cover 964 to recycle or dispose of the needle holder 20 at a more convenient time. According to another embodiment, the user can restock the cells 960 with unused pen needles 30. Embodiments of the present invention may be used to provide portable, personal sharps containers that allow for safe disposal of contaminated sharps and may improve needle disposal compliance of needle users. In addition, embodiments of the present invention entirely remove the sharps portion of an injection device and retain the needle inside, while allowing the user to recycle or discard the plastic non-sharps component as regular trash. Further, with embodiments of the present invention, users do not need to replace their sharps containers frequently due to the low volume occupied per needle. Additionally, storage units themselves may be made significantly smaller than prior art sharps containers, thus making them more convenient and portable. This convenience may result in increased sharps disposal compliance. Moreover, complicated electronics are not required. Readily available power sources, such as AA or 9V batteries, or button cell batteries can be used for personal, portable needle removable storage devices in accordance with embodiments of the present invention.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

What is claimed is:

1. An apparatus for removing a needle from a needle holder, comprising:
   a grasping unit comprising arms for grasping the needle, each arm having at least one tapered portion;
   a receiving unit for receiving the needle holder, at least one of said grasping unit and said receiving unit being displaceable with respect to the other of said grasping unit and said receiving unit;
   a biasing unit biasing at least one of said grasping unit and said receiving unit in a first direction; and
   separating means for separating the entire needle from the needle holder; wherein the receiving unit comprises an activating unit comprising an annular disk, which upon displacement of the displaceable one of said grasping unit and said receiving unit in a second direction opposite to the first direction, engages the tapered sections of the arms, thereby automatically causing the arms to grasp the needle;
   wherein upon separation of the entire needle from the needle holder, the biasing unit automatically displaces the displaceable one of said grasping unit and said receiving unit in the first direction, thereby displacing the annular disk relative to the tapered arm portions and reducing the engagement therewith, thereby automatically releasing said separated needle;
   wherein adhesive connects the needle with the holder; and
   the separating means heats the needle to melt, soften, or otherwise weaken material and/or adhesive connecting the needle with the needle holder.

2. The apparatus according to claim 1, wherein the grasping unit includes a chamber for receiving the needle separated from its holder.

3. The apparatus according to claim 1,
   wherein the separating means comprises an electrical circuit completed by the needle; and
   wherein current flowing through the electrical circuit melts, softens, or otherwise weakens the material and/or adhesive connecting the needle with the needle holder, allowing the displaceable one of said grasping unit and said receiving unit to displace in the first direction under the bias of the biasing unit while arms of the grasping unit grasp the needle, to separate the needle from the needle holder.

4. The apparatus according to claim 3, wherein a pair of electrical contacts are respectively disposed on a pair of the arms of the grasping unit, and
   wherein the needle completes the electrical circuit when grasped by the arms.

5. The apparatus according to claim 3, further comprising a cover selectively connectable to the grasping unit, the cover having a first electrical contact;
   wherein one of the arms has a second electrical contact disposed thereon; and
   wherein subsequent to displacing the displaceable one of said grasping unit and said receiving unit in the second direction, thereby causing the arms of the grasping unit to grasp a second end of the needle, upon connecting the cover to the grasping unit, the first electrical contact contacts a first end of the needle and completes the electrical circuit through the needle.

6. The apparatus according to claim 3, further comprising a cover selectively connectable to the grasping unit, the cover having an internal protrusion;
   wherein one of the arms has a first electrical contact disposed thereon;

wherein the receiving unit comprises a second electrical contact biased away from the needle and selectively displaceable through the receiving unit; and wherein subsequent to displacing the displaceable one of said grasping unit and said receiving unit in the second direction, thereby causing the arms of the grasping unit to grasp the needle, upon connecting the cover to the grasping unit, the protrusion displaces the second electrical contact to contact the needle, completing the electrical circuit through the needle.

7. The apparatus according to claim 6, wherein the second electrical contact comprises a spike that cuts through the needle holder to contact the needle.

8. The apparatus according to claim 6, wherein the second electrical contact comprises a resistive heating element that burns or melts through the needle holder to contact the needle.

9. The apparatus according to claim 8, wherein the resistive heating element comprises a nichrome wire.

10. The apparatus according to claim 8, further comprising a third electrical contact disposed on the receiving unit for contacting the needle and providing an additional current path through the needle.

11. The apparatus according to claim 3, wherein the grasping unit further comprises a resistive heating element comprising a blade simultaneously contacting the needle to complete the electrical circuit through the needle and cutting and melting or burning through the needle holder.

12. The apparatus according to claim 1, further comprising a needle dispenser integrated with the apparatus.

13. An apparatus for removing a needle from a needle holder, comprising:

a grasping unit comprising arms for selectively grasping the needle, each arm having at least one tapered portion;

a receiving unit for receiving the needle holder, at least one of said grasping and receiving units being displaceable with respect to the other of said grasping and receiving units;

a biasing member biasing at least one of said grasping and receiving units in a first direction away from the other of said grasping and receiving units;

a separator for separating the entire needle from the needle holder; and a storage unit for storing the separated needle;

wherein the receiving unit comprises an activating unit comprising an annular disk, which upon displacement of the displaceable one of said grasping unit and said receiving unit in a second direction opposite to the first direction, engages the tapered sections of the arms, thereby automatically causing the arms to grasp the needle;

wherein upon separation of the entire needle from the needle holder, the biasing unit automatically displaces the displaceable one of said grasping unit and said receiving unit in the first direction, thereby displacing the annular disk relative to the tapered arm portions and reducing the engagement therewith, thereby automatically releasing said separated needle;

wherein adhesive connects the needle with the holder; and the separator heats the needle to melt, soften, or otherwise weaken material and/or adhesive connecting the needle with the needle holder.

\* \* \* \* \*